United States Patent [19]

Yoon

[11] Patent Number: 4,535,773

[45] Date of Patent: Aug. 20, 1985

[54] SAFETY PUNCTURING INSTRUMENT AND METHOD

[76] Inventor: InBae Yoon, 2101 Highland Ridge Dr., Phoenix, Md. 21131

[21] Appl. No.: 362,410

[22] Filed: Mar. 26, 1982

[51] Int. Cl.³ .............................................. A61B 17/34
[52] U.S. Cl. ..................... 604/51; 128/630; 128/653; 128/753; 604/118; 604/169
[58] Field of Search ............... 128/630, 653, 748, 753, 128/754; 604/118, 121, 164–170, 272–274

[56] References Cited

U.S. PATENT DOCUMENTS

| | | | |
|---|---|---|---|
| 1,147,408 | 7/1915 | Kells | 128/374 |
| 1,213,001 | 4/1917 | Philips | 128/374 |
| 1,835,287 | 12/1931 | Donovan | 128/374 |
| 2,097,039 | 10/1937 | Peterson | 128/374 |
| 2,496,111 | 1/1950 | Turkel | 128/754 |
| 2,525,329 | 10/1950 | Wyzenbeek | 128/374 |
| 2,541,542 | 2/1951 | Perez et al. | 128/374 |
| 2,623,521 | 12/1952 | Shaw | 128/754 X |
| 3,007,471 | 11/1961 | McClure, Jr. | 128/2 |
| 3,459,189 | 8/1969 | Alley et al. | 128/214 |
| 3,540,447 | 11/1970 | Howe | 128/374 |
| 3,545,443 | 12/1970 | Ansari | 128/374 |
| 3,565,074 | 2/1971 | Foti | 604/170 X |
| 3,613,684 | 10/1971 | Sheridan | 128/374 |
| 3,789,852 | 2/1974 | Kim | 128/374 |
| 3,817,250 | 6/1974 | Weiss et al. | 128/374 |
| 3,860,006 | 1/1975 | Bhupendra | 128/374 |
| 3,895,632 | 7/1975 | Plowiecki | 128/374 |
| 3,993,079 | 11/1976 | de Gatztanondo | 128/374 |
| 3,994,287 | 11/1976 | Turp et al. | 128/374 |
| 4,013,080 | 3/1976 | Froning | 128/374 |
| 4,177,814 | 12/1979 | Knepshield et al. | 128/374 |
| 4,180,068 | 12/1979 | Jacobsen et al. | 128/374 |
| 4,186,750 | 2/1980 | Bhupendra | 128/374 |
| 4,215,699 | 8/1980 | Bhupendra | 128/374 |
| 4,254,762 | 3/1981 | Yoon | 128/4 |
| 4,299,230 | 11/1981 | Kubota | 128/748 |
| 4,345,589 | 8/1982 | Hiltebrandt | 128/4 |

Primary Examiner—Edward M. Coven
Attorney, Agent, or Firm—Robert E. Bushnell

[57] ABSTRACT

A surgical instrument 10 having a normally closed valve assembly 20 at its proximal end 28 which may be manually opened to receive an implement 40 terminating in a sharp blade 46 and point 48 for puncturing the wall 82 of an anatomical cavity 84. During penetration of a cavity wall, an inner sleeve 56 or a blunt probe 354 is depressed. The depression provides a tactile signal sensible to a surgeon holding the instrument and, in conjunction with an anciliary electronic network 110, causes a visual and aural ready signal to be emitted. Upon completion of a cavity wall puncture, the inner sleeve 56 or blunt probe 354 is released, thereby shielding interior anatomical structure from the sharp implement point 48 and providing a tactile signal while simultaneously triggering the electronic network to generate a visual and aural signal indicating completion of the puncture.

55 Claims, 58 Drawing Figures

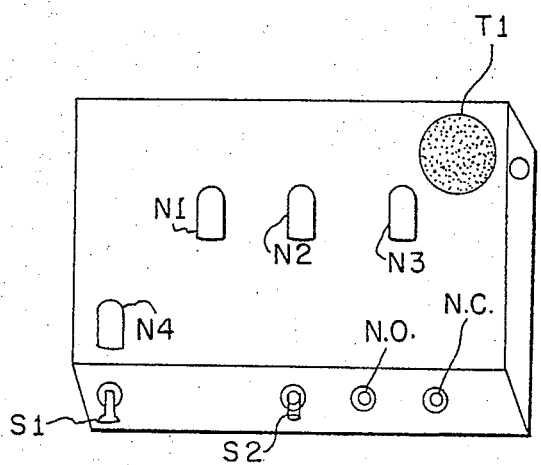
FIG.6
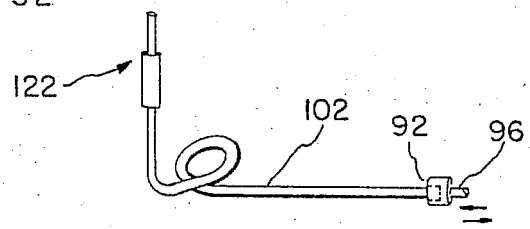
FIG.7A
FIG.7C
FIG.7B
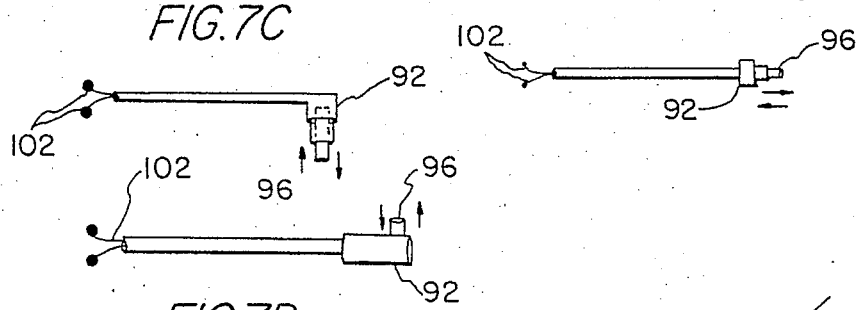
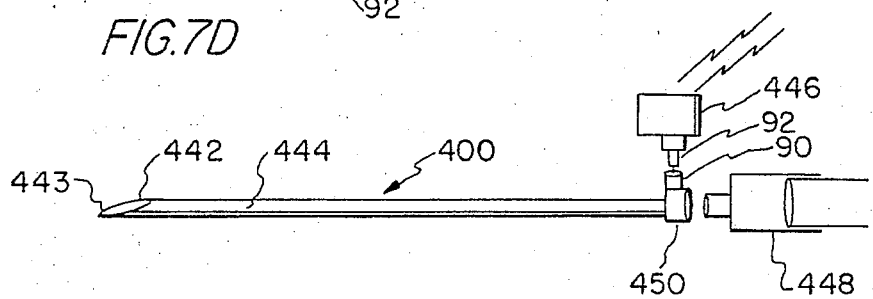
FIG.7D
FIG.32

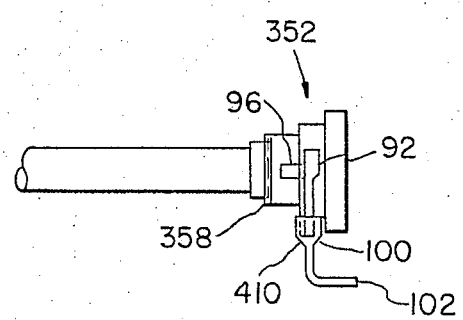
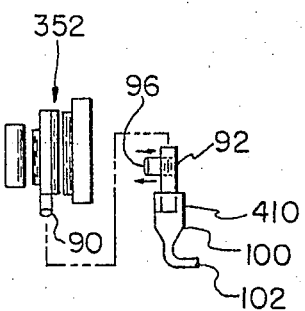
FIG.29A    FIG.29B
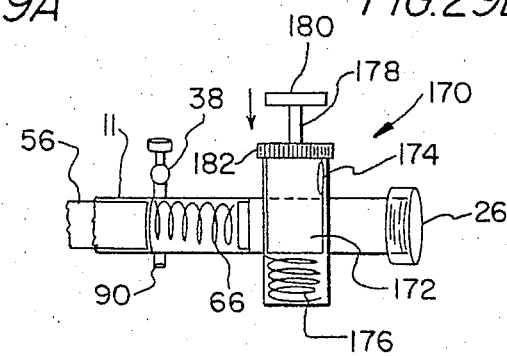
FIG.14
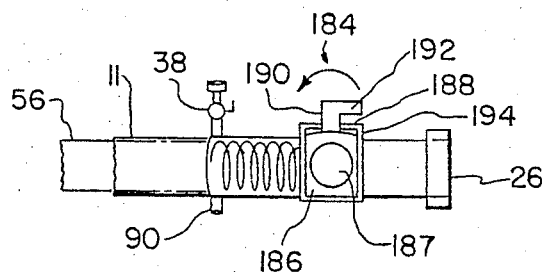
FIG.15
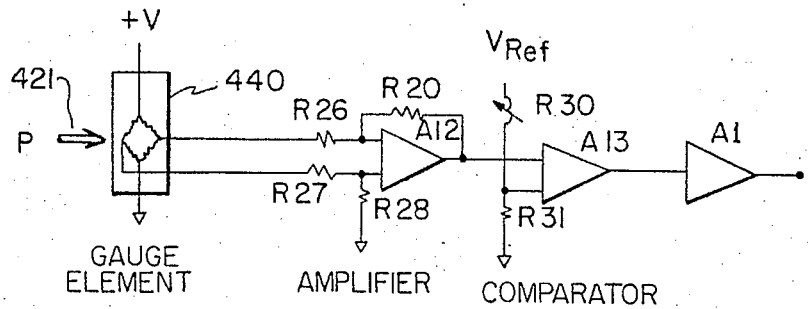
FIG.31E

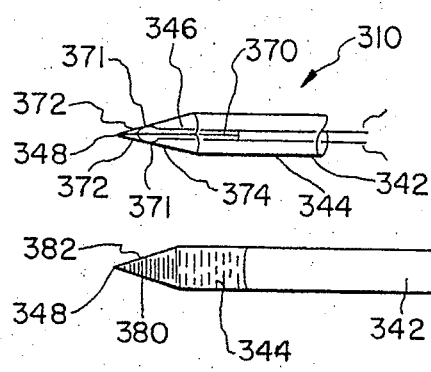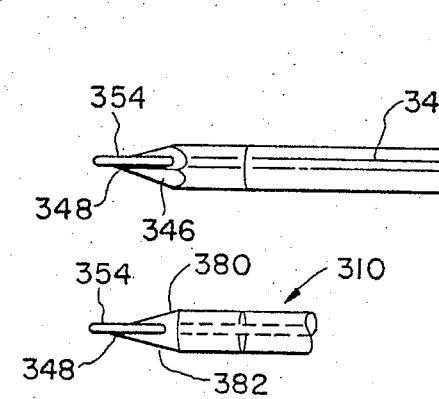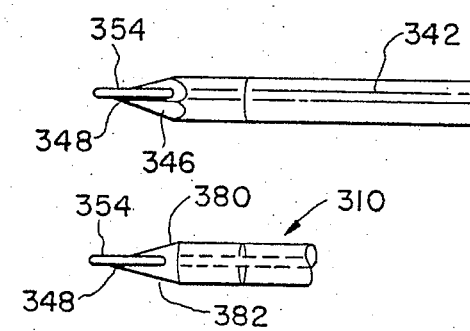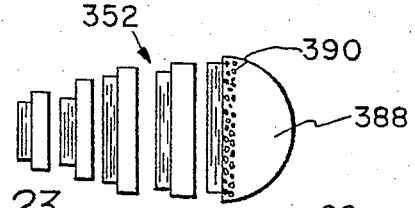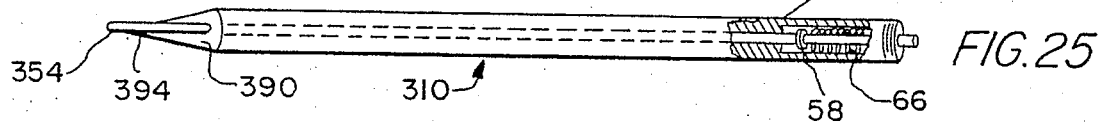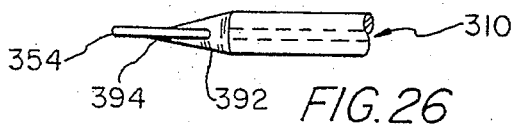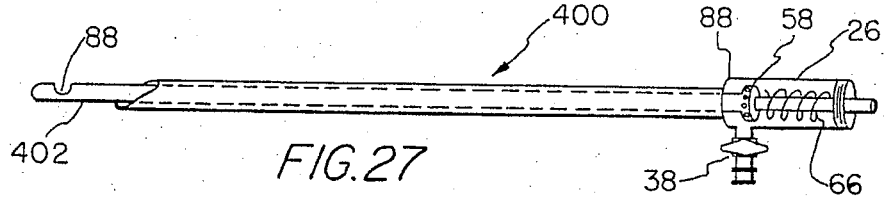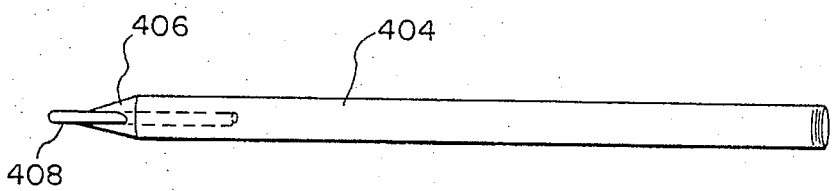

SAFETY PUNCTURING INSTRUMENT AND METHOD

TECHNICAL FIELD

This invention relates to surgical instruments and, more particularly, to instruments and methods in which a sharp implement pierces or punctures an anatomical cavity to provide communication with the inside of the cavity.

BACKGROUND ART

Many medical procedures gain access to the inside of an anatomical cavity by using an implement such as a trocar, cannular or needle having a sharpened point to pierce or puncture the bodily tissues, muscles and membranes forming the cavity wall. A surgical needle, for example, connected to a catheter may be used to pierce a cavity (blood vessel, subarachnoid space, heat ventricle). After piercing the cavity, the needle is left in situ and used to inject or withdraw gaseous or liquid phase fluids from the cavity. Similarly, in several endoscopic procedures, a small incision may be made in the skin of a patient along the abdomen for example, and the sharp point of a larger penetrating implement such as a trocar of suitable length and diameter is inserted into the incision, and pushed until the point punctures the cavity wall. Then, a sleeve is slid over the exterior surface of the implement into the puncture wound to serve as a lining for preserving the shape of the passageway created by the implement. After the sleeve is in place, the implement may be withdrawn and an endoscope and operating instruments may be inserted via the sleeve to view and operate upon organs within the cavity.

Penetrating the wall of an anatomical cavity with a surgical puncturing instrument can be quickly done and, usually creates a small neat passageway providing communication to the interior of the cavity. While the sharp point of a penetrating implement is being pushed through a cavity wall, it encounters great resistance from the tissue, muscle and membranes forming the cavity wall. Once the sharp point and blade of the implement pass through the cavity wall and into the cavity, the resistance drops significantly. The sharp point of the implement, however, can easily injure organ structure within the cavity upon the slightest contact. Unless a surgeon stops pushing the implement just as soon as penetration is complete, there is a grave risk that the implement will continue penetrating deeply into the cavity and injure neighboring organ structure. If an unintended bodily member is injured by the point of the implement, unless an immediate and massive hemorrhage occurs, the injury may not become apparent until long after completion of the surgery. At a minimum, such an injury will delay a patient's recovery and may seriously endanger the patient's health. Corrective surgery may be required.

Some aspects of the dangers presented by the sharpened point of a penetrating implement have been previously recognized by those skilled in the field of surgical puncturing instruments.

U.S. Pat. No. 1,213,001 for example, positions a flat rubber cup along the outside of a cannula to limit the depth of trocar penetration. Additionally, a section of the proximal end trocar shaft is threaded whereby a threaded runner or lock-nut may be moved along the threaded shaft section to vary the extent by which the trocar point will protrude beyond the distal end of the cannula.

Similarly, U.S. Pat. No. 3,613,684, although using a trocar with a blunt, rounded tip, discloses an adjustable collar which fits around the exterior circumferential surface of the trocar shaft. The collar limits the extent of penetration of the trocar into a patient's body and provides a surgeon with a visual indication of the extent of penetration.

Another instrument, disclosed in U.S. Pat. No. 3,817,250, has a puncturing needle for performing a tracheostomy. The puncturing needle passes through the proximal end of a wide collar. The distal end of the collar forms a bearing surface against the neck of a patient at an acute angle to the longitudinal axis of the needle, thereby limiting the extent of penetration of the puncturing needle into the patient.

Devices such as cannula cups and collars are intended to be set prior to use to limit penetration into a bodily cavity to a single, fixed depth. The depth of penetration necessary to reach the inside of an anatomical cavity or to puncture an organ inside an anatomical cavity differs, however, for different organs. The depth of penetration necessary to reach a particular organ also differs among patients, being influenced by factors such as age, degree of development, obesity, sex, and previous medical experience. An instrument providing a fixed depth of penetration is, therefore, unsuitable for general surgical use because, for different patients, different thicknesses of tissue lie between the surface skin and the interior wall of an anatomical cavity. Even if the position of cannula collar is adjustable, the instrument provides no advance assurance that a particular setting will be adequate to permit the implement to reach the organ desired or that the depth of penetration will prevent the implement from penetrating too far into a cavity or organ and injuring neighboring anatomical members. Moreover, the collars only indicate the preset limit upon the depth of penetration and fail to provide a surgeon with a contemporaneous indication of whether the implement has successfully punctured the desired cavity after it has reached the preset limit of penetration. Some instruments have attempted to address the danger created by excessive penetration by providing a graduated scale on the cannula to indicate to a surgeon actual depth reached by the sharpened implement point. The visual indication provided, however, is independent of the depth of penetration necessary to reach a particular organ. Other instruments, the spinal epidural anesthetic needle taught in U.S. Pat. No. 4,215,699 for instance, rely upon changes of relative pressure differentials communicated to a sealed testing device chamber at the proximal end of the instrument to determine the location of the penetrating implement tip. Although the latter instrument provides a contemporaneous indication when the needle tip reaches a desired depth and a different indication when excessive penetration occurs, it is limited in use to the subarachnoid space. Both types of instruments rely upon a visual indication to appraise a surgeon about the relative depth of penetration; they provide only marginal protection against excessive penetration and no protection against post-penetration injury to the patient from inadvertent contact between neighboring organs and the sharp tip of the penetration implement.

Furthermore, none of the presently available surgical instruments provide protection to a patient against the sharp point of the penetrating implement after the implement has successfully penetrated a cavity. Until the point of the implement is withdrawn from a wound by retraction into the cannula, the possibility of an inadvertent contact between the point of the implement and other organs or membranes creates a serious risk that the point will graze, cut or even puncture other internal members of the patient.

Often, a preliminary precautionary procedure is taken, particularly prior to penetration of the pelvic or abdominal cavities, in an effort to reduce the risk of injuring interior anatomical structures. After a small incision is made, a needle such as the Verres needle or a small diameter safety endoscope of the type disclosed in U.S. Pat. No. 4,254,762 for instance, is first used to puncture the cavity wall. A gas, $CO_2$, is next introduced into the cavity to create pneumoperitoneum, causing the cavity wall to bulge outward and separate from the organ structure inside the cavity. Then, a larger implement such as a trocar may be used to puncture the cavity wall with a lower risk of injuring other organ structure subsequent to penetration. Despite this precautionary procedure, there are still significant incidents of injury to bowels, blood vessels, and omenta due to inadvertent contact with the sharp trocar blade.

STATEMENT OF THE INVENTION

Accordingly, it is one object of the present invention to provide a safer surgical instrument for puncturing an anatomical structure.

It is also an object to provide a simpler apparatus to protect patients from the dangers presented by piercing and puncturing surgical instruments.

It is another object to provide a mechanism to automatically shield a sharp point of a surgical puncturing instrument after the point has penetrated an anatomical structure.

It is yet another object to provide a mechanism to shield a sharp point of a surgical puncturing instrument when the point is not penetrating an anatomical structure.

It is still another object to provide a surgical instrument having a sharp point for puncturing anatomical organ structures with a mechanism for shielding the point after penetration of an anatomical organ structure.

It is a further object to provide a device to supply a signal when a sharp point of a surgical instrument successfully penetrates an anatomical cavity.

These and other objects are achieved with a surgical puncturing instrument such as a trocar, cannula or needle, having a mechanism biased to automatically protrude from the distal end of the instrument and shield its sharp, penetrating point after the point has punctured an anatomical organ cavity. The bias force applied to the mechanism is weak enough to permit the mechanism to recede and expose the sharp point when the distal end of the longitudinal instrument is pressed against the wall of an anatomical structure, but sufficiently strong to protrude beyond the sharp point after the instrument has passed through the cavity wall. While protruding, the mechanism shields the sharp point and prevents the point from contacting or grazing and thereby injuring anatomical structures inside the punctured cavity. Additionally, the surgical instrument may be made sensitive to passage of the point of a penetration implement through an organ structure and fitted with a switch for triggering a sensible signal to alert a surgeon when the point has punctured the cavity wall. The signal may be tactile, aural, or visual.

BRIEF DESCRIPTION OF THE DRAWINGS

A more complete appreciation of this invention, and many of the attendant advantages thereof, will be readily apparent as the same becomes better understood by reference to the following detailed description when considered in conjunction with the accompanying drawings in which like numbers indicate the same or similar components, wherein:

FIG. 6 is a view of an enclosure for the electrical alarm network shown in FIG. 5.

FIGS. 7A through 7D show alternative configurations of switches which may be used to connect the alarm network of FIG. 5 to a safety puncturing instrument.

FIG. 14 is a cut-away section front view of an alternative puncturing instrument valve assembly.

FIG. 15 is a cut-away sectional front view of an alternative puncturing instrument valve assembly.

FIG. 20 shows a front view of an alternative puncturing implement.

FIG. 21 shows a front view of an alternative puncturing implement.

FIG. 22 shows a front view of an alternative puncturing implement.

FIG. 23 shows a front view of an alternative handle for a puncturing implement.

FIG. 24 shows a front view of an alternative puncturing implement.

FIG. 25 shows a front view of an alternative puncturing implement.

FIG. 26 shows a front view of an alternative puncturing implement.

FIG. 27 shows a front view of an alternative puncturing implement.

FIG. 28 shows a front view of an alternative puncturing implement.

FIGS. 29A and 29B show front and assembly views of an electrical switch fitted into a puncturing implement handle.

FIGS. 31A through 31E show various alternative arrangements of sensor switch mechanisms which may be incorporated into cavity puncturing instruments to activate a penetration progress indicating network.

FIG. 32 shows a wireless penetration progress indicating radio frequency transmitted plug coupled directly to the structure of a cavity puncturing instrument.

DETAILED DESCRIPTION OF THE INVENTION

Figure 1:
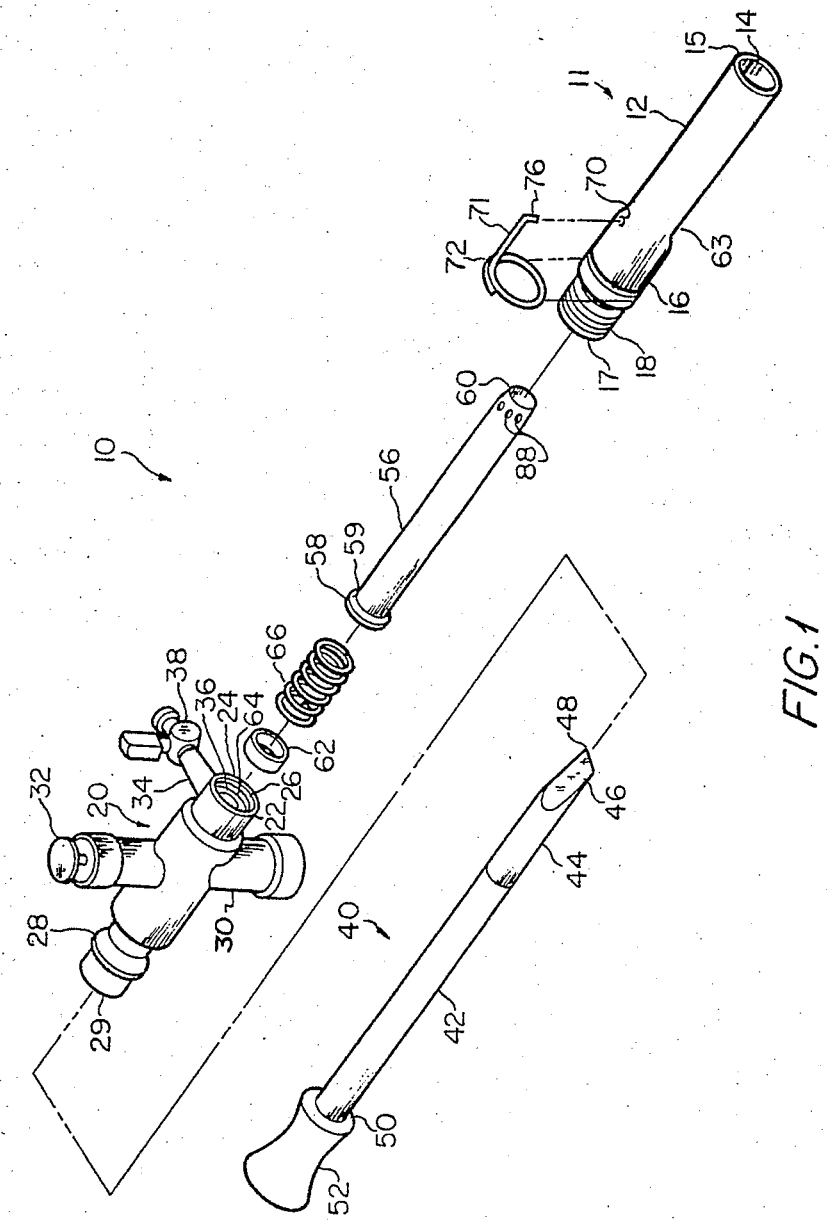
FIG. 1 is an exploded isometric view of one embodiment of the present invention.

Referring now to the drawings, FIG. 1 illustrates a surgical instrument, generally designated by numeral 10, dedicated to puncturing an anatomical organ structure such as a cavity wall and providing a passageway via the puncture wound for communicating with the interior of the cavity. The instrument 10 has an outer cylindrical sleeve 11 having an elongated section 12 with an interior lumen 14 opening into a distal end 15 and extending through to its proximal end 17. Sleeve 11 may have an enlarged cross-section 16 at its proximal end 17 terminating in a male threaded coupling 18. A commercially available valve assembly 20 such as the trumpet valve shown, is connectable to the proximal end of the sleeve 11 to prevent the egress or escape of fluids from the cavity via the sleeve. The distal end 22 of assembly 20 contains a female threaded coupling 24 for receiving the male threaded section 18 of outer sleeve 11. The assembly contains a lumen 26 open at its distal end 22 and extending through to its proximal end 28. A flexible seal 29 having a central aperture coaxial with lumen 26, of a resilient material such as rubber may be fitted onto the proximal end 28. The intermediate section of assembly 22 contains a trumpet valve 30 of the type disclosed in greater detail in U.S. Pat. No. 3,989,049, which is slidably operable perpendicularly to the longitudinal axis of lumen 26. Typically, the trumpet valve contains a gate that is held by spring loading in a position to block passage of liquid or gaseous phase fluids through lumen 26. Manual depression of finger button 32, however, counteracts the spring loading on the gate and permits communication between the distal and proximal ends of lumen 26. The intermediate section also contains an anesthetic connection port 34 opening into lumen 26 at junction 36. Passage of fluids through the port may be controlled or blocked completely by a stop-cock 38.

A trocar 40, having a long shaft 42 terminating at its distal end 44 in a three-sided blade 46 of surgical steel forming a sharp point 48, may be introduced into the proximal end 28 of lumen 26 of valve assembly 20 via the central aperture in the rubber seal 29. After the gate of valve assembly 20 is opened, the shaft 42 and sharp point 46 of trocar 40 may be pushed longitudinally forward through lumina 26 and 14 when the shaft 42 has been fully inserted into lumina 26 and 14, the forward rim 50 of a knob 52 attached to the proximal end of trocar 40 will abut against the outer rim of the rubber seal 29; the blade 46 and sharp point 48 will extend beyond the distal end 15 of sleeve 11.

A thin-walled inner sleeve 56 having a flange 58 connected by a sloped shoulder 59 at its proximal end and a tapered distal end 60 of reduced cross-section, may be placed inside the outer sleeve 11 before outer sleeve 11 is screwed together with valve assembly 20. The tapered distal end 60 should form a thin, blunt bearing surface. When pushed toward the distal end 15 of outer sleeve 11, the flange 58 will seat against the junction 63 between the lesser 12 and greater 16 cross-sections of sleeve 11. The reduced cross-section of the distal end 60 of inner sleeve 56 should form a close fit against the circumferential surface of the distal end 44 of trocar 40. A collar 62 may be inserted into lumen 26 and seated against a ridge 64 inside the lumen. A compression spring 66 may be positioned between the collar 62 and flange 58 as outer sleeve 11 is joined to valve assembly 20. After the outer sleeve 11 and valve assembly 20 are joined, spring 66 will be housed inside the enlarged cross-section 16 of outer sleeve 11. The compression load applied by spring 66 on flange 58 will force the distal end 60 of inner sleeve 56 to protrude from lumen 14 beyond the distal end 15 of outer sleeve 11. The length of inner sleeve 56 should be sufficient to completely shield the blade 46 and point 48 when the shaft 42 of trocar 40 is fully inserted into lumina 14, 26.

A small hole 70 may be drilled through the wall of outer sleeve 11 at the point where the flange 58 seats against the junction 63 between the lesser 12 and greater 16 cross-sections. A small diameter, stiff wire 71 may be wound into one or two loops 72 as a tension spring and fitted around the circumference of the greater cross-section 16 of the outer sleeve. A groove 74 may be cut into the circumference of the greater cross-section 16 to receive and hold the loops of wire 71 stationary relative to the circumferential surface of outer sleeve 11. The tip 76 of wire 71 may be bent radially inward so as to extend into junction hole 70. Wire 71 should be bent slightly inward along its length so as to bias the tip 76 to extend radially inward through junction hole 70. The length of tip 76 should be greater than the wall thickness of greater cross-section 16 so that when flange 58 is pushed forward to seat against the interior wall of junction 63, sloped shoulder 59 forces tip 76 radially outward and onto the rim of flange 58. When flange 58 is seated against the interior wall of junction 63, the flange holds up 76 radially outward. The bias force applied by wire 71 on tip 76 will normally hold the tip 76 radially inward. Then, when inner sleeve 56 is forced rearward against spring 66 and toward the proximal end of outer sleeve 11, the bias on tip 76 will force the tip radially inward. The radial movement of tip 76 provides a tactile signal indicative of the position of flange 58 and, thus, the position of the distal end 60 of sleeve 56 relative to the distal end 15 of the outer sleeve 11 and, when a trocar is fully inserted into lumina 14, 60, to the blade and point of the trocar.

Figure 2A:
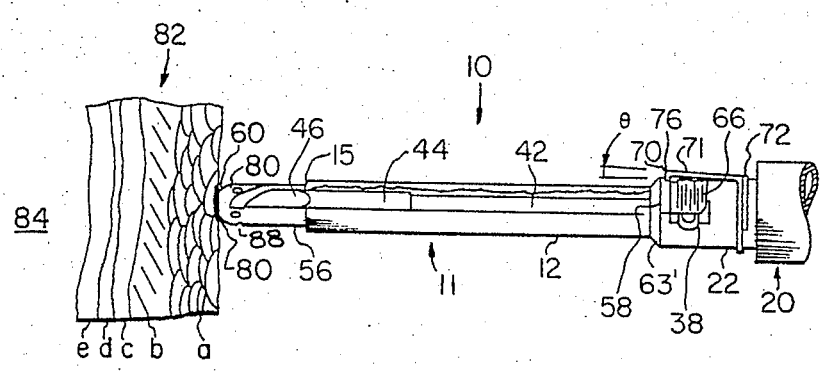
FIGS. 2A through 2D show, in sequential diagrammatic sectional views, an embodiment of the present invention in use to puncture an anatomical cavity wall of a patient.
Figure 2B:
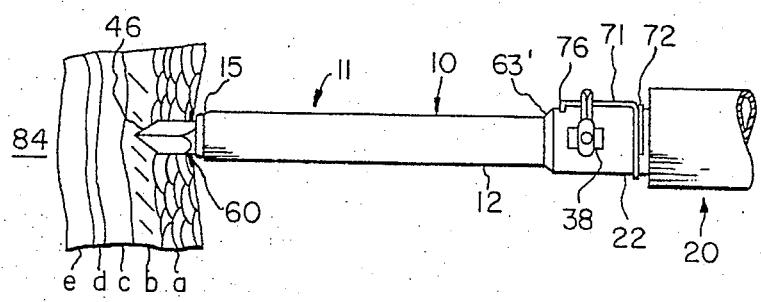
Figure 2C:
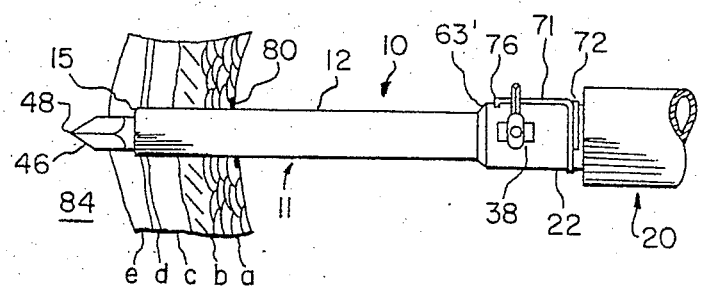

Turning now to FIGS. 2A through 2D, a small incision 80 may be made in the surface layer of skin "a" of the wall 82 of an anatomical cavity of a patient in preparation for use of a puncturing instrument 10. The blunt distal end 60 of the inner sleeve 56 may then be placed against the incision 80 as is shown in FIG. 2A. When the instrument is in this position, spring 66 holds inner sleeve 56 fully extended so that its distal end 60 protrudes beyond and covers the trocar blade 46 and point 48; the flange 58 is seated against the inner surface of junction 59, thus holding the tip 76 of the tactile sense wire radially outward at an angle θ with the circumference of the surface of the distal end 22 of valve assembly 20. Force manually applied to the proximal end (not shown) 52 of the trocar 40 by pushing proximal end 52 with the palm of a hand. When proximal trocar end 52 is pushed to the left, the blunt distal end 60 is held in place by resistance of the cavity wall 82 while the abutment of trocar rim 50 on the distal end 28 and rubber seal 29 of the valve assembly 20 forces outer sleeve 11 and trocar blade 46 to the left, thereby opening a puncture wound in the cavity wall as shown by FIGS. 2B and 2C. Consequently, as the force applied on the proximal end of the trocar pushes the outer sleeve 11 against the incision 80, the distal end 60 of inner sleeve 56 is forced inside of the distal end 15 of outer sleeve 11, compressing spring 66 between a proximal interior rim of chamber 22 and the flange 58 of the inner sleeve 56 and permitting the tip 76 of inwardly biased tactile spring 71 to pop into hole 70. When the outer sleeve 11 enters into the puncture wound, the inner sleeve 56 is held completely inside the outer sleeve 11, as shown in FIG. 2C, by the resistance of the cavity wall to passage of the distal ends 15, 60 of the outer and inner sleeves. If force continues to be applied to the proximal end of the trocar, point 48 and blade 46 of the trocar will pass through the cavity wall 82 and enter into anatomical cavity 84. The force applied to the proximal end of the trocar causes entire instrument 10, including outer sleeve 11, to follow through the wound.

Figure 2D:
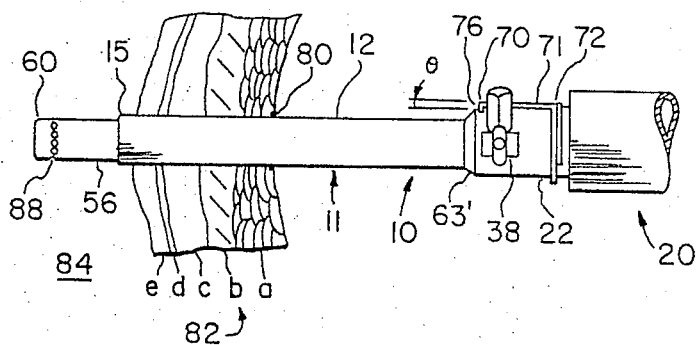

Just as the distal ends 15, 60 clear the inner surface layer "e" of the cavity wall, the resistance of the cavity wall to movement of inner and outer sleeves 11, 56 drops significantly in magnitude, suddenly releasing the inner sleeve 56 to the force of compressed spring 66. When released, the distal end 60 of inner sleeve 56 moves to the left relative to blade 46 and the distal end 15 of the outer sleeve 11, completely encasing blade 46, point 46 at the distal end 44 of the trocar as shown in FIG. 2D. This action effectively shields the interior of anatomical cavity 84 immediately after passage of the sharp point 48 and blade 46 through the cavity wall and protects any organs or other anatomical structure within the cavity from incidental contact or grazing by the blade 46 or sharp point 48 of the trocar. The normal force applied by spring 66 to the inner sleeve 56 should be adequate to cause the inner sleeve to remain fully extended beyond trocar point 48 in all circumstances except when significant force is intentionally applied to the proximal end of the trocar. Simultaneously with the release of the distal end 60 of the inner sleeve 56, flange 58 moves to seat against the inner surface of junction 63', causing the ramp 59 adjoining the flange to force the tip 76 of the tactile sensor 71 radially outward. When flange 58 is seated against junction 63', tip 76 rests on the rim of the flange and the length of tactile sensor wire 72 protrudes upward from the surface of distal end 22 by an angle θ.

The instantaneous movement of the distal end 15 of the outer sleeve 11 to clear the inner layer "e" of the cavity wall, release of inner sleeve 56 to completely encase the trocar blade 46, and the outward movement of tactile sensor 71 simultaneously shields the anatomical structure of the patient from the trocar blade 46 and gives the surgeon with a sensible signal (which will be immediately felt by one of the surgeon's fingers) that the puncture wound is complete, thus alerting the surgeon to stop pushing the trocar. Once the cavity wall 82 has been punctured, stop-cock 38 may be turned from a closed position, shown in FIG. 2C, to an open position, shown in FIG. 2D, to permit the admission of a fluid such as gaseous phase carbon dioxide for insufflation of the anatomical cavity 84. The gas will travel between the interior wall of inner sleeve 56 and the portion of recessed diameter of trocar shaft 42, and enter into cavity 84 via inner sleeve ports 88. Alternatively, trocar 40 may be removed from lumina 14, 60 allowing the gate (not shown) of the valve assembly 20 to seal the proximal end of lumen 14 while or even before fluid is being admitted via stop-cock 38.

Figure 3:
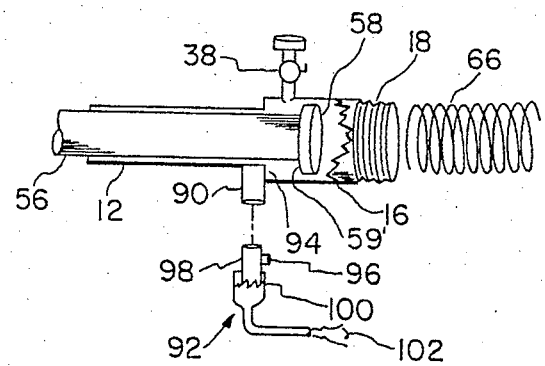
FIG. 3 is a cut-away sectional view showing the sensor assembly of the proximal ends of inner and outer sleeves of a safety puncturing instrument.

It may be noted that the design of the connection between the distal end chamber 22 of valve assembly 20 and the proximal end of outer sleeve 11 is not limited to a single configuration. In FIG. 1, for example, the outer sleeve 11 has a proximal section of greater diameter 16 to accommodate the inner sleeve flange 58, compression spring 66, and tactile sensor 71. In FIGS. 2A–2D, however, greater diameter section 16 is not necessary because distal end chamber 22 is slightly longer and able to accommodate flange 58 and spring 66. In FIG. 3, however, the greater diameter section 16 is modified to include a socket 90 capable of receiving a plug couplable electrical switch 92. Socket 90 has an interior opening 94 to the interior of section 16 through which a normally protruding plunger 96 may be actuated by movement of the radial shoulder 59' of the inner sleeve flange 58. When inserted into socket 90, plunger 96 is manually held depressed inside the body 98 which encapsules the switch contacts (not shown). Switch body 98 fits snugly inside socket 90 and a sheath 100 around the outer circumference of the switch body will fit tightly around the outside of the socket, thereby sealing the socket against passage of any fluids. Switch 92 may contain contacts for two or more electrical leads 102.

Figure 4A:
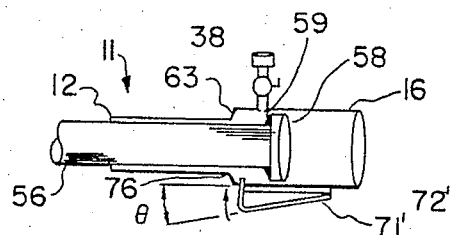
FIG. 4A is a top cut-away sectional view showing an alternate sensor assembly at the proximal ends of the inner and outer sleeves.
Figure 4B:
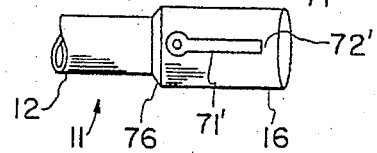
FIG. 4B is a front sectional view of the assembly shown in FIG. 4A.

FIGS. 4A and 4B illustrate an alternative arrangement of the proximal end of outer sleeve 11 with a lever arm 71' serving as a tactile sensor to indicate whether the flange 58 and sloped shoulder 59 are seated against the inner surface of junction 63. When flange 58 is seated against junction 63, the lever arm 71' is forced outward by an angle θ, thereby giving a tactile signal that the distal end of the inner sleeve 56 is fully protruding beyond the distal end of the outer sleeve. The proximal end 72' of the lever arm 71' may be attached to section 16 by spot welding.

Figure 5:
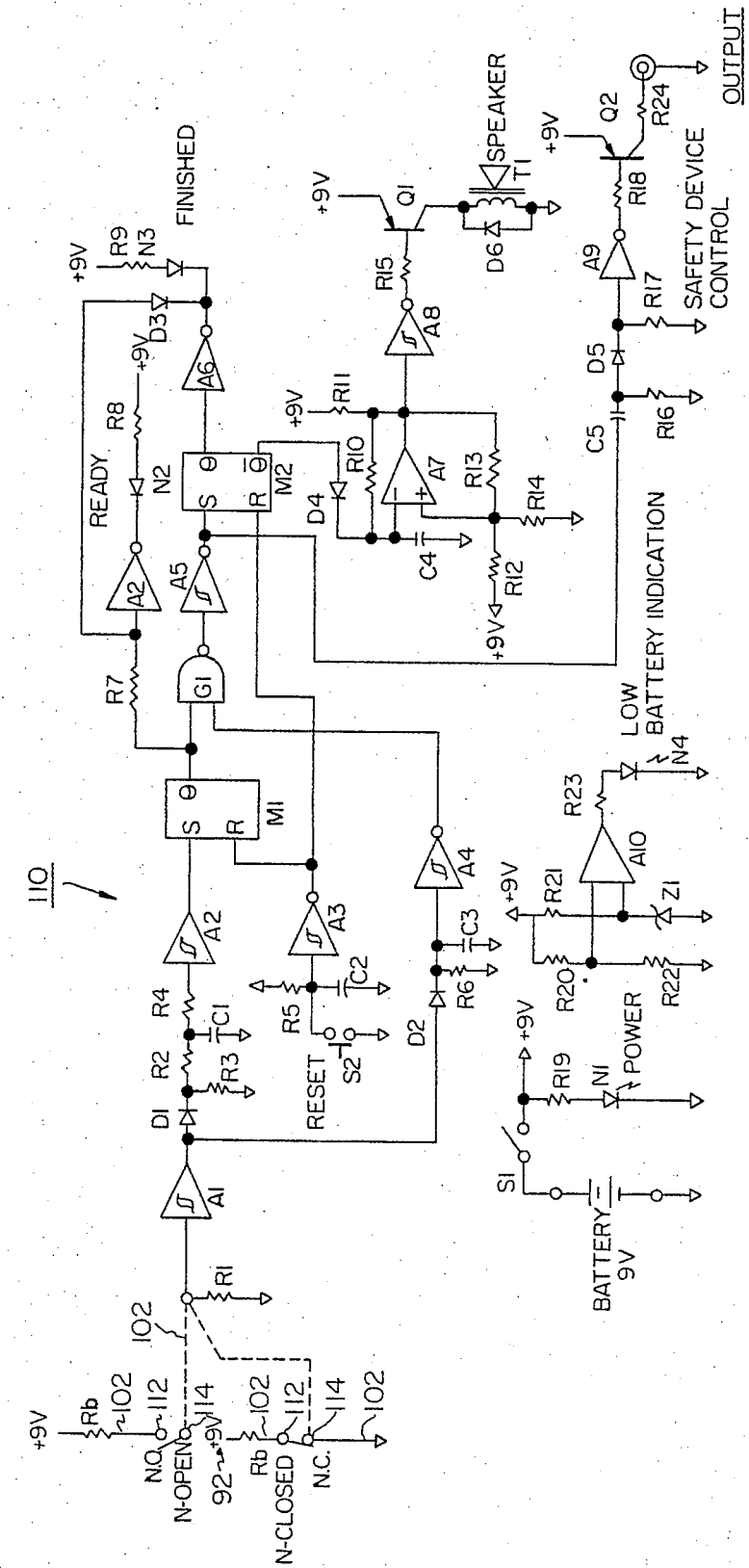
FIG. 5 is an electrical schematic diagram of an alarm network usable in conjunction with a safety puncturing instrument.

Electrical switch 92 may have either a normally open or normally closed contact configuration. FIG. 5 illustrates both configurations of switch 92 coupled via leads 102 to a typical electronic alarm network 110 suitable for use with a puncturing instrument 10 to advise a surgeon about the operation of the instrument during penetration. One contact 112 of the switch is connectable through resistance Rb to a battery. The other contact 114 is connectable across resistance R1 to a buffer amplifier A1. Current from the output terminal of amplifier A1 is divided across two branches. One branch, via a time delay bridge of diode D1, resistances R2, R3, and R4 and capacitance C1, and amplifier A2, toggles the set "S" terminal of multivibrator M1, which, in turn, feeds one terminal of logic gate G1. The second branch, via a time delay bridge of diode D2, resistance R6 and capacitance C3, and amplifier A4, feeds the other terminal of logic gate G1. Gate G1 is coupled via operational amplifier A5 to the set "S" terminal of multivibrator M2.

When the network is to be used, switch 92 is first securely plugged into the socket 90 on a sterile penetrating instrument. Normally open switch 92 will be held in a closed position by the flange 58 of the inner sleeve 56 when the inner sleeve is in its normal or rest position fully protruding beyond the distal end 15 of the outer sleeve. Switch S1 is then closed to couple a battery to the network 110. When switch S1 is closed, voltage across resistance R19 causes light emitting diode N1 to emit light, providing a visual signal that the network is energized. Then, when normally opened sensor switch 92 is closed (or, when normally closed sensor switch 92 is opened) in response to rearward movement of the flange 58 of the inner sleeve toward the proximal end 18 of the outer sleeve when instrument 10 is pressed against an anatomical cavity wall 84 in the manner shown in FIG. 2B, the application of voltage to (or removal from) switch terminal 112 causes multivibrator M1 to hold a voltage on one terminal of logic gate G1. This also establishes a voltage difference across light emitting diode N2, causing diode N2 to emit light, a second visual indication. Both diodes N1 and N2 emit light while the inner sleeve 56 is held toward the proximal end of the outer sleeve during passage of the distal end 15 of the outer sleeve through an anatomical cavity wall 82.

Subsequently, normally open sensor switch 92 is again forced closed (or, normally closed switch 92 is again forced open) by movement of the flange 58 to seat against junction 63 when a puncture of the cavity wall 82 is completed and the inner sleeve is released to its rest position. This change in the condition of sensor switch 92 toggles logic gate G1 and the signal applied to the set "S" terminal of multivibrator M2, resulting in a completed circuit through light emitting diode N3. This causes diode N3 to emit light, a third visible indication about the operation of instrument 10. The toggling of multivibrator M2 also activates an oscillator circuit of diode D4, capacitance C4, resistances R10, R11, R12, R13, R14, and amplifier A7 wich, via amplifier A8 and resistance R15, controls the base of transistor Q1. The oscillator circuit thus causes a sinusoidal current to flow between the emitter and collector of transistor Q1 through a speaker circuit of diode D6 and speaker T1. Consequently, speaker T1 emits an aural signal which indicates the release of inner sleeve 56 upon completion of the puncture. Activation of diode N3, speaker T1, and wire 71 simultaneously provides a visual, aural, and an independent tactile alarm signal that the trocar blade 46 has successfully completed a puncture and that the surgeon should immediately cease efforts to push the trocar deeper into the wound.

The human tissue, skin and membrane which forms a cavity wall 82 is very resilient and tends to oppose passage of a puncturing implement such as trocar, cannula or needle. Occasionally a surgeon will pause in the application of force while pushing a puncturing instrument through a cavity wall. When this happens, the resilience of the cavity wall tends to push the blade 46 of the puncturing implement and the outer sleeve 11 of the instrument in the opposite direction (to the right in FIG. 2C, for example), thereby releasing the inner sleeve 56 to protrude partially or completely beyond the distal end 15 of the outer sleeve. If inner sleeve protrudes almost completely, its flange 58 will activitate the tactile sensor lever 71 and sensor switch 92, causing the network 110 to emit the visual signal of diode N3 and the audio signal of speaker T1, thereby falsely indicating that puncture of the cavity wall is complete. A surgeon is very aware whenever he pauses in his application of force prior to completion of a puncture and is readily able to correct the false alarm by instructing the circulating nurse to push reset switch S2 before resuming efforts to push the implement through the cavity wall. Switch S2 manually resets multivibrators M1 and M2 via their reset "R" terminals. Some types of plug couplable switches 92, that shown in FIG. 3, for instance, will have their contacts forced from the normal condition when the switch is inserted into socket 90, causing diode N2 to emit light if switch S1 is closed. Then, as switch 92 is fully inserted, its plunger 96 may release switch contacts to their normal condition if the inner sleeve flange 58 is not seated against junction 63', thereby causing diode N3 to emit light and speaker T1 radiate a sound. By pressing reset switch S2, these false signals may be canceled, leaving lit only diode N1 (to indicate that network 110 is energized) and, if flange 58 is not seated, diode N2 (to indicate that inner sleeve distal end 60 is pushed toward the proximal end). Network 110 may additionally equipped with a circuit of zener diode Z1, resistances R20, R21, R22 and R23, and operational amplifier A10 which will illuminate light emitting diode N4 when the voltage of the network battery becomes discharged.

As shown in FIG. 6, the alarm network 110, including its battery, may be conveniently packaged in a small, shirt-pocket sized plastic or metal mini-box 120. Light emitting diodes N1, N2, N3 may be aligned in a row on one surface of the box and, may radiate different colors, perhaps red, yellow and green, respectively. Speaker T1 and low-voltage light emitting diode N4 may be located at other positions on the same surface. Switches S1 and S2 may be located on one side alongside sockets for receiving jacks 122 connected to normally open (N.O.) and normally closed (N.C.) configured sensor switches 92. One surface of the mini-box may be fitted with a shirt-pocket clip (not shown) so that the alarm network may be routinely carried by a surgeon and by means of sterile, disposible switch 92 and jack 122 sets, coupled to different puncturing instruments as the need arises.

Figure 8:
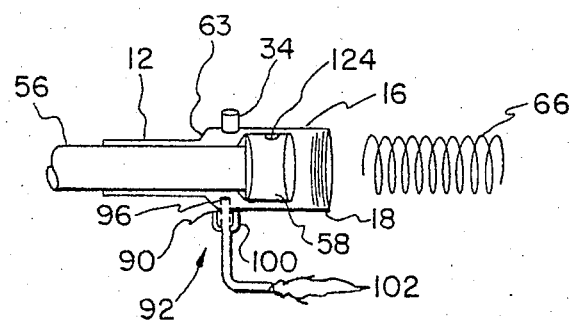
FIG. 8 is a cut-away sectional view showing the arrangement of inner and outer sleeves in conjunction with an alarm network switch.

FIGS. 7A through 7D illustrate several different configurations of sensor switches 92 which may be connected to various types of socket receptacles 90 on puncturing instruments. Different arrangements of one or more switches and various sophisticated alarm networks may be used with particular designs of puncturing instruments. FIG. 8 illustrates one such arrangement where a switch 92 with a vertical contact plunger 96 is operated by axial movement of a sloped shoulder 59 in conjunction with the flange 58 at the proximal end of an inner sleeve.

FIG. 8 also illustrates an alternative arrangement of the greater diameter section 16 of the outer sleeve 11 in which the electrical socket 90 is symmetrically arranged diametrically opposite the insufflation port 34. To accommodate the location of the insufflation port 34 at the junction 63, the flange 58 of the inner sleeve is perforated with one or more apertures 124 to allow fluids to pass between the hollow inner sleeve and port 34. If only one aperture 124 is used and a close fit between the outer circumference of flange 58 and inner circumference of section is desired, inner sleeve 56 should be keyed to outer sleeve 11 to maintain alignment between port 34 and aperture 124.

Figure 9:
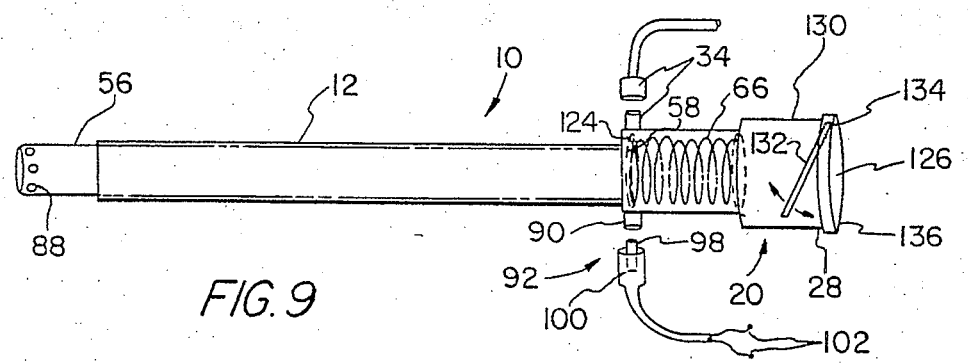
FIG. 9 is a cut-away front view showing the arrangement of a safety puncturing instrument with an alternative valve assembly.
Figure 10:
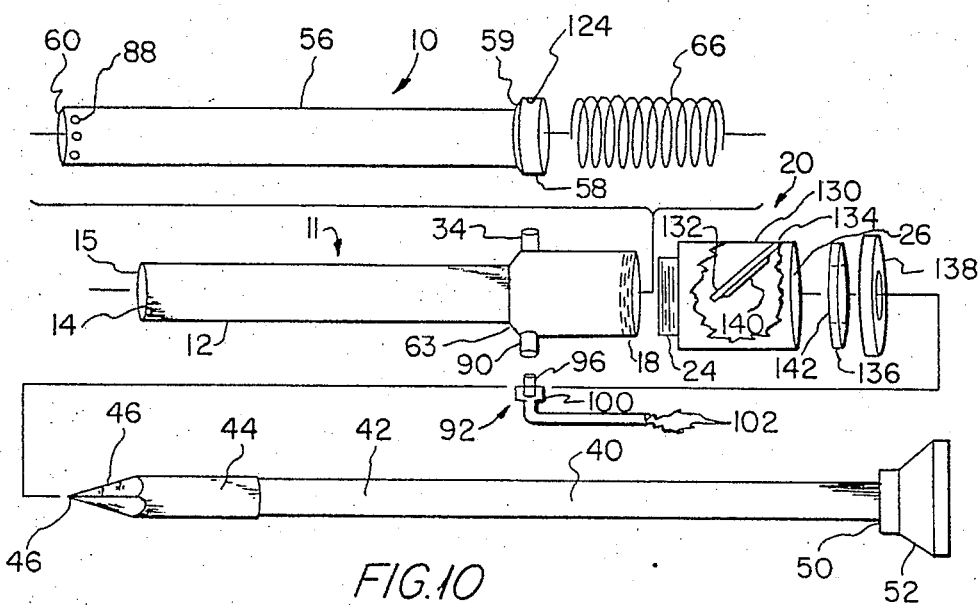
FIG. 10 is an exploded front view showing the arrangement of a safety puncturing instrument with an alternative valve assembly.

FIGS. 9 and 10 illustrate a puncturing instrument 10 having an alternative valve assembly 130 in which a circular gate 132 is biased by a compression spring hinge 134 to form a tight fit against a compliant gasket 136 held in place by a threaded washer 138 at the proximal end 28 of the assembly. Gate 132 may be attached to the proximal end 28 by means of the spring hinge 134. The gate 132 may be fitted with a magnet 140 conforming in shape to the aperture 142 in gasket 136 and gasket 136 may be made of a ferromagnetic material so that magnetic attraction between gate 132, magnet 140 and gasket 136 assures an air-tight valve closure when trocar 40 is removed from lumen 26. Gate 140 may be opened for insertion of trocar 40 simply by pressing the trocar point 44 against magnet 140.

Figure 11:
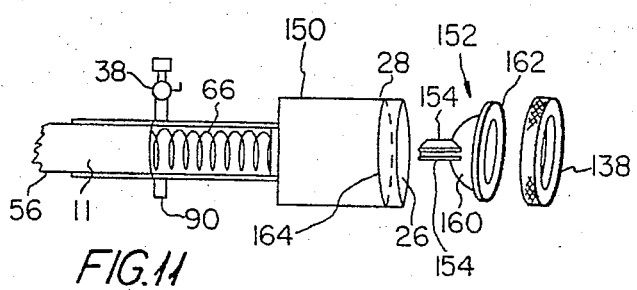
FIG. 11 is a cut-away sectional views of an alternative puncturing instrument valve assembly.
Figures 12A, 12B, 12C:
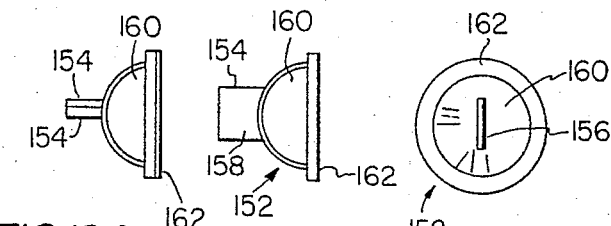
FIGS. 12A through 12C are side, front, top and side views, respectively of an alternative puncturing instrument valve.

FIG. 11 illustrates an alternative valve assembly 150 in which a nipple 152, shown in greater detail in the planar views of FIGS. 12A, 12B and 12C, is inserted into the proximal end 28 of the valve assembly to serve as an air-tight gate. Nipple valve 152 has a pair of planar flaps 154 forming either side of a single teat 156. Flaps 154 are attached along parallel arcs 158 to the bowl 160 of the nipple. The bowl 160 terminates with a flange 162 which rests against an internal shoulder 164 inside the proximal end of assembly 150. A threaded washer holds nipple 152 in place inside the valve assembly 150. A trocar 40 may be inserted in lumen 26 merely by pushing the trocar point 46 into the bowl 160 and through teat 156; the teat and flap form a tight seal against the trocar shaft 44 which conforms to its circular cross-sectional shape. Upon withdrawal of the trocar, teat 156 closes and flaps 154 come together, thereby sealing lumen 26 to passage of fluids via the valve assembly. Nipple valve 152 may be made of a rubber, teflon or plastic material, with or without imbedded magnetic particles.

Figure 13:
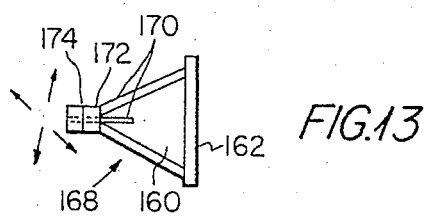
FIG. 13 is a cut-away sectional front view of an alternative puncturing instrument valve.

An alternative embodiment of a nipple valve 168, shown in FIG. 13, has a conical bowl 160 terminating in a quadrature split teat 170. The flaps 172 of the quadrature teat 170 are held together by an expandable ring 174. Nipple valve 168 may be made of a rubber, teflon or plastic material, with or without imbedded magnetic particles.

FIG. 14 illustrates a two sleeve puncturing instrument having an alternative valve assembly 170. The valve has a cylindrical gate 172 having a transverse axial passage 174 held out of axial alignment with lumen 26 by a compression spring 176 so that the body of the cylindrical gate 172 blocks lumen 26. A valve stem 178 supporting a manually operable finger button 180 arises through a threaded cap 182. This allows a surgeon to depress the finger button 180, forcing gate 172 against spring 176 until gate passage 174 is in axial alignment with lumen 26 to permit entry of a trocar shaft 42.

FIG. 15 illustrates a two sleeve puncturing instrument havng an alternative valve assembly 184. The valve has a cylindrical gate 186 with a traverse axial passage 187 rotatably held out of axial alignment with lumen 26 by a coiled spring 188. A valve stem 190 having a lever 192 arises through a threaded cap 194. A surgeon may rotate lever 192, rotating stem 190 and valve gate 186 against spring 194 until gate passage 187 is in axial alignment with lumen 26 to permit entry of a trocar shaft 42.

Figures 16A, 16B:
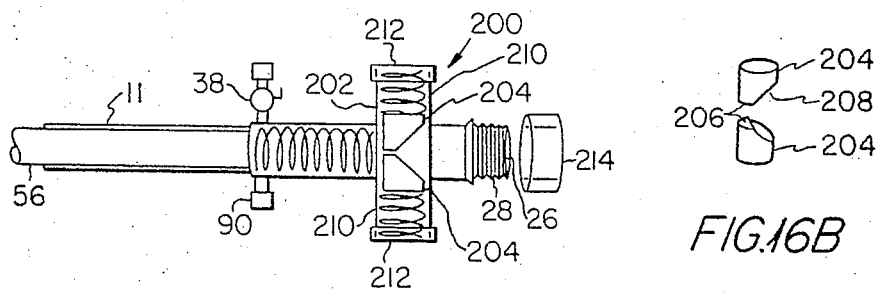
FIGS. 16A and 16B show a sectional view of an alternative valve assembly.

FIGS. 16A and 16B illustrate a two sleeve puncturing instrument having an alternative valve assembly 200. The valve has a central cylindrical chamber 202 having diametrically opposite ends at right angles to the longitudinal axis of lumen 26. A pair of matching cylinders 204 are positioned in axial alignment inside chamber 202 with facing bases 206 truncated by wedged surfaces 208. The matching cylinders are held inside chamber 202 with their wedged surfaces 208 oriented towards the proximal end 28 of lumen 26. The facing bases 206 are held against one another by a pair of springs 210 placed inside opposite ends of chamber 202. Threaded caps 212 close the ends of chamber 202. A trocar may be inserted into lumen 26 by pusing the trocar blade against the wedged surfaces 208, an action which will force the matching cylinders apart against springs 210 to admit the trocar.

Figure 17:
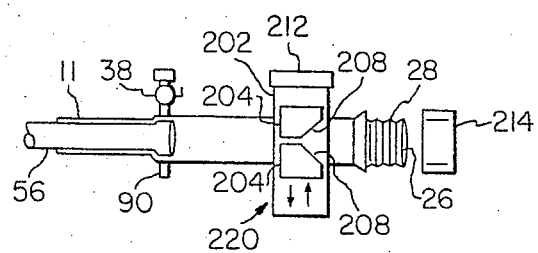
FIG. 17 shows a cut-away view of an alternative valve assembly.
Figure 28B:
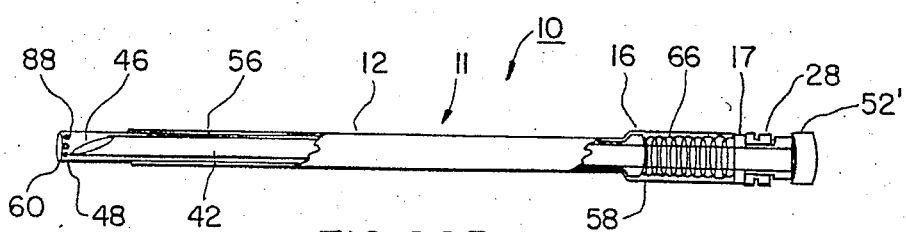
FIGS. 28B through 28E show alternative embodiments of safety puncturing instruments.
Figure 28C:
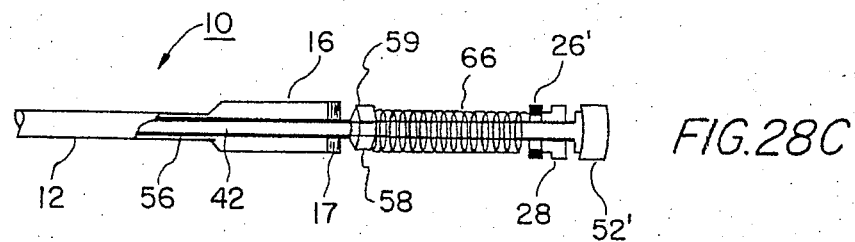
Figure 28E:
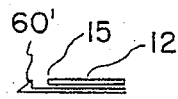
Figure 28D:
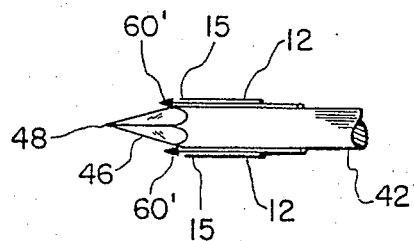

FIG. 17 illustrates a two sleeve puncturing instrument having an alternative valve assembly 220. The valve has a central cylindrical chamber 202 having diametrically opposite ends at right angles to the longitudinal axis of lumen 26. A pair of matching cylinders 204' made of a magnetic material and having opposite facing polarities are positioned in axial alignment inside chamber 202 with facing wedged surfaces held in orientation towards the proximal end 28 of lumen 26. A threaded cap 212 closes one end of chamber 202. A trocar may be inserted into lumen 26 by pushing the trocar blade against the wedged surfaces 208. A sealing cap 214 of a rubber or teflon may be placed over the proximal end 28 of the valve assembly.

Figure 18:
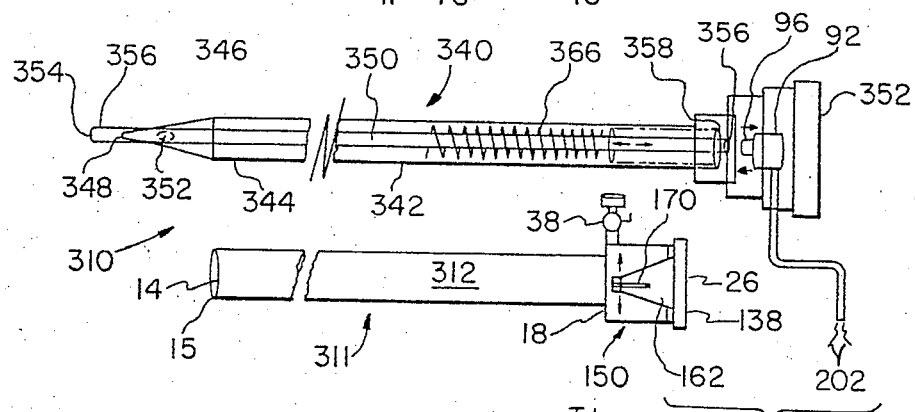
FIG. 18 shows an assembly view of an alternative puncturing implement.
Figure 19:
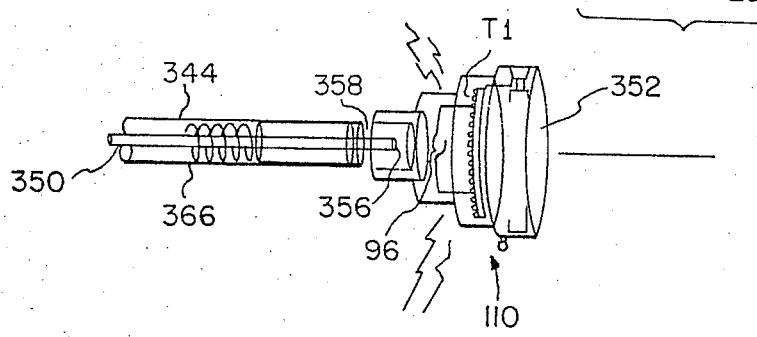
FIG. 19 shows a sectional view of the proximal end of an alternative puncturing implement.

FIGS. 18 and 19 illustrate an alternative embodiment of a safety puncturing instrument. This embodiment 310 has a single sleeve 311 with a cylindrical member 312 having a valve assembly 150 at its proximal end 18. Valve assembly 150 contains a nipple valve 162 for sealing lumina 14, 26 against passage of air or gaseous phase fluids. A trocar 340 having a sharp conical blade 346 and point 348 at its distal end 344 may be pushed through a quadrature teat 170 in the nipple valve and inserted into lumina 14, 26. A solid rod 350 extends along the trocar shaft 342 and protrudes from the side of trocar blade 346 through a hole 352. The tip 354 of rod 350 should be beveled to present a surface flush with the surface of the trocar blade 346 when the rod is fully depressed into trocar shaft 342 while penetrating an anatomical cavity wall. The proximal end 356 of the rod extends beyond the proximal end 358 of the trocar shaft 342. A compression spring 366 inside the trocar shaft biases the rod 350 so that the distal rod tip 354 normally protrudes beyond the sharp trocar point 348.

During penetration of an anatomical cavity wall, the resistance caused by the tissue, muscle and membranes forming the wall depress the rod 350 against spring 366 with its tip 354 flush against the surface of trocar blade 346, thereby fully exposing the sharp trocar point 348. During penetration, the proximal end 356 of rod depresses a plunger 96 in an electrical switch fitted into the head 352 attached (e.g., by screw threads) to the proximal end 358 of the trocar shaft 342. The switch may be coupled via electrical leads 202 to an electronic network 110 providing visual and aural alarm signals. Depression of switch plunger activates a ready signal (e.g., N2) in the electronic network. As soon as trocar blade 346 punctures the inner layer of a cavity wall, the lack of cavity wall resistance releases rod 350 to the action of spring 366, which, in turn, causes rod tip 354 to protrude beyond the distal trocar point 348, thereby shielding the interior anatomical structure of a cavity from inadvertent injury by the distal end of the trocar. Protrusion of rod tip 354 also causes forward movement of the rod proximal end 356, thereby releasing switch plunger 96 to activate a puncture completed signal (e.g., N3 and speaker T1) in the electronic network 110. As shown in FIG. 19, the entire electronic network, including its battery and aural alarm speaker T1 may be fitted into the trocar head 352 which may be attached by screw threads to the proximal end 358 of a sterile trocar shaft before surgical use.

FIG. 20 illustrates an alternative trocar 310 having four (two shown) spring wires 370 protruding from the trocar blade 346. The distal tips 372 of the springs 370 are bent outward into loops 371 and connected to the surfaces of the trocar blade 346. The proximal ends of spring wires 370 extend along the inside of the trocar shaft 342 and protrude beyond the proximal shaft end (not shown) where the proximal spring ends may activate the plunger 96 of an electrical sensor switch. During penetration of a cavity wall, the bent distal ends 371 of spring wires 370 are depressed into grooves 374 in the trocar blade surface. Depression causes the spring wires to lengthen and move towards the proximal end where they may, in turn, depress the plunge 96 of a sensor switch, thereby causing an alarm network to indicate a ready (e.g., N2 lit) condition. Then, when a puncture is completed, loops 371 and switch plunger are released, causing the network to indicate a puncture completed condition (e.g., N3 lit and T1 activated).

FIG. 21 illustrates an alternative trocar 310 terminating in a conical surface 380 bearing male threads 382. The trocar shaft 342 may be made hollow. The handle 352 attached by screw threads to the proximal trocar shaft end 358, is made with several inter-threaded disks of increasingly larger diameter. An alarm network including a speaker T1 may be fitted into the handle.

FIG. 22 illustrates an alternative trocar 310 terminating in a multi-sided sharp blade 346 from the side of which a spring-loaded blunt probe 354 protrudes from the trocar blade 346 to shield the sharp trocar tip 348. The handle 352 may have its largest diameter disk 386 formed into a hemispherical dome 388, shown in FIG. 23, with perforations 390 around its edge to allow sound emission.

FIG. 24 illustrates an alternative embodiment of a trocar 310 having a conical surface 380 bearing male threads 382. A spring-loaded blunt probe 354 protrudes from an opening in the trocar surface 380 to shield the sharp trocar tip 348.

FIG. 25 illustrates an alternative trocar 310 terminating in an off-center pyramid blade 390 positioned off axial center to allow a blunt probe 354 to protrude through the center of the blade. FIG. 26 illustrates an alternative trocar 310 having an off-center conical surface 392 positioned off axial center to allow a blunt probe 354 to protrude through the center of the blade and shield the point 394 of the blade.

FIG. 27 illustrates an alternative puncturing implement 400 with a configuration suitable for use as a surgical needle. A spring-loaded blunt probe 402 remains extended except during penetration through a cavity wall. During penetration the probe retracts, producing a completely flat surface. While retracted, the probe depresses the plunger of a sensor switch located in a handle, causing an alarm network to exhibit a ready signal (e.g., N2 lit). Relase of the blunt probe upon completion of a puncture causes the network to exhibit a warning alarm (e.g., N3 lit, T1 sounding). FIG. 28 illustrates an alternative puncturing implement 404 terminating in a tipless cone 406 through which a probe 408 extends. FIGS. 29A and 29B illustrate an alternative configuration of the handle 352 of a puncturing implement. In this configuration, an electrical sensor switch may be fitted into the handle and a removable jack 410, having a surrounding sheath 100, may connect the switch 92 to electrical leads 102.

Figure 30:
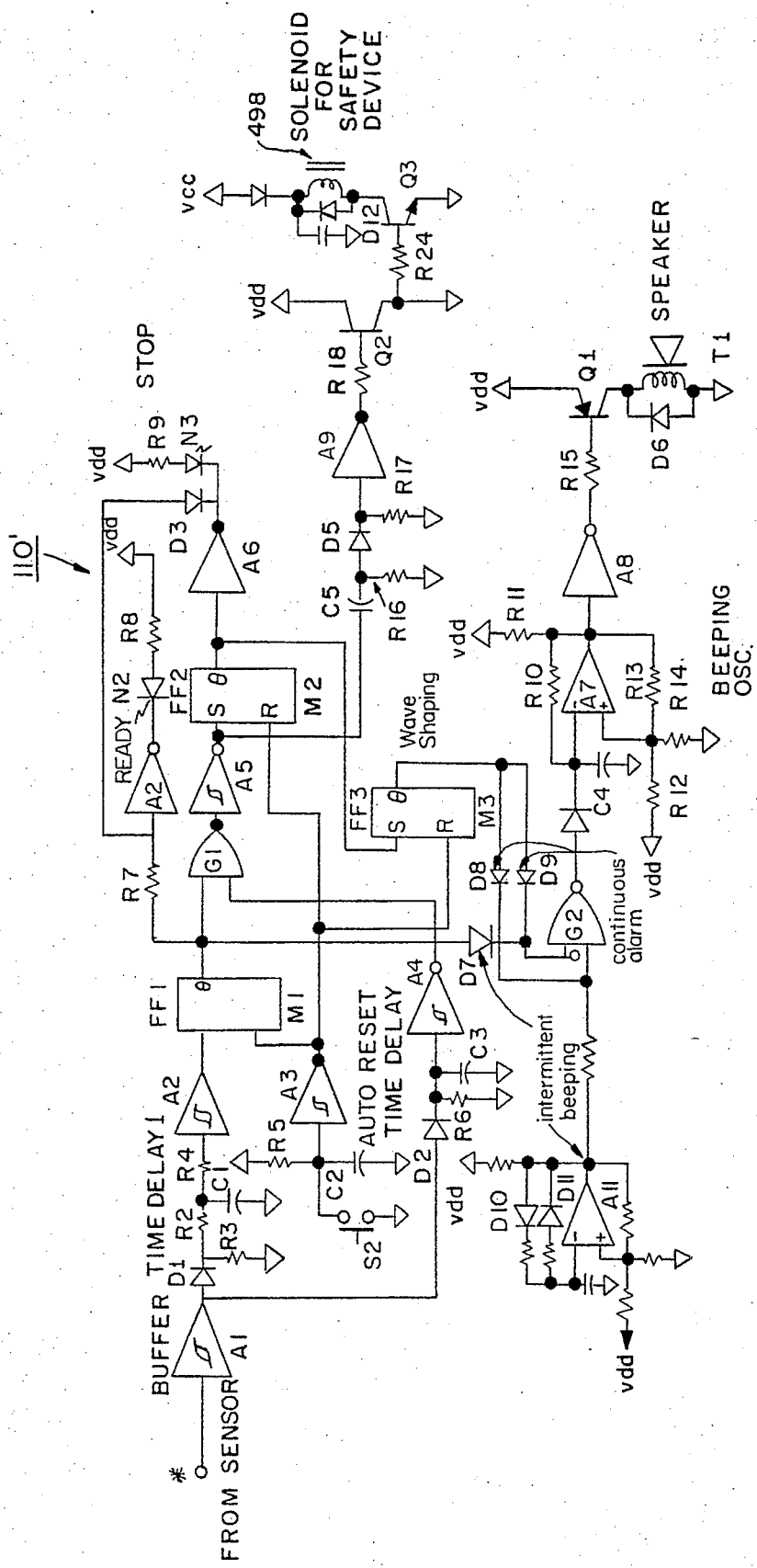
FIG. 30 is a schematic diagram of an alternative electronic alarm network.

As indicated by the alternative network illustrated in FIG. 30, the aural signal generated by network 110 to indicate completion of a puncture may be either a steady or intermittent tone, a melodic sound or a record segment of human speech. The network may be modified to generate an intermittent tone during the ready condition to complement the visual signal emitted by diode N2 during penetration and then generate a steady, louder tone upon completion of the puncture.

It may be noted that the principles disclosed herein are applicable to surgical puncturing implements such as trocars, cannulas, and needles of different diameters and lengths.

Figure 31A:
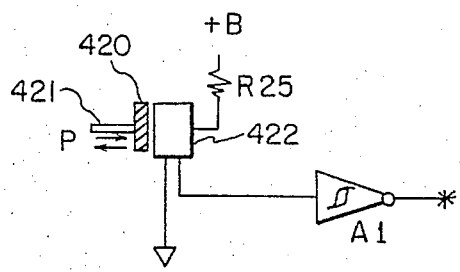
Figure 31C:
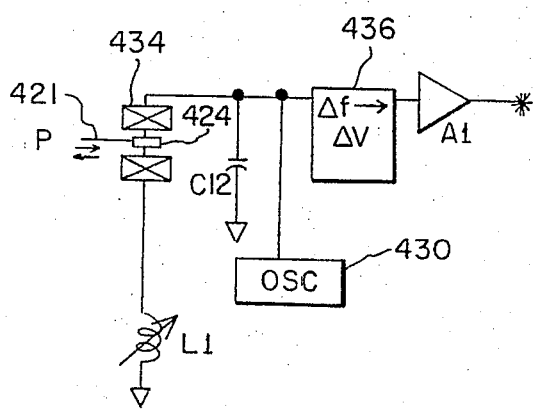
Figure 31D:
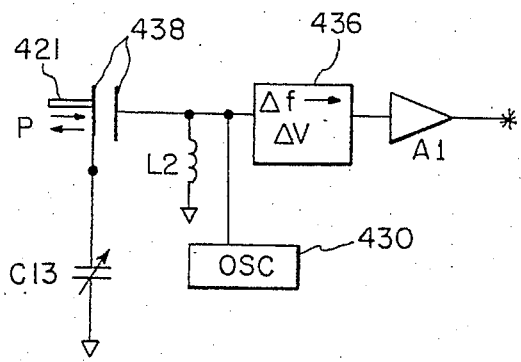
Figure 31B:
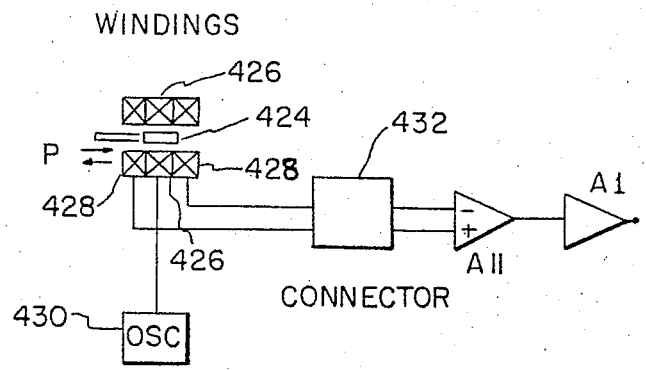

In addition to the mechanical sensors switches 92 shown in conjunction with use of the networks of FIGS. 5 and 30, several other types of electrical and magnetic mechanisms, shown in FIGS. 31A through 31E, may be substituted for the mechanical switch 92. These other switches may also be activated by reciprocating motion of either a second sleeve 56 in a puncturing instrument 10 or by a probe 354 or spring wire 371 protruding from the tip or blade of a sharp pointed puncturing implement 40, 310, 400, 404 within an instrument. FIG. 31A, for example, shows a magnet 420 controlled by motion of reciprocating element 421 to control a magnetic sensor 422. The sensor 422, in turn, is coupled via resistance R25 between a battery and a local ground to control buffer amplifier A1. FIG. 31B shows a magnetic conductor 424 controlled by motion of a reciprocating element 421 to modulate the balance of magnetic flux between coil winding 426 positioned between a pair of balanced sensor coil windings 428. Coil winding 426 is coupled to an oscillator 430. Sensor coil windings 428 are coupled via connector 432 to opposite polarity terminals of a comparator amplifier A11 wherre reciprocation of conductor 426 may be detected as a disturbance of magnetic flux balance between the coil windings. FIG. 31C shows a magnetic conductor 424 controlled by motion of a reciprocating element 421 to change the resonance within an annular coil winding 434. Resonance is determined by a capacitance C12 coupled in parallel with an oscillator 430. The coil winding 434 is coupled to a circuit 436 for converting changes in frequency to changes in voltage. The converter circuit 436 is, in turn, coupled to an input terminal of buffer amplifier A1. A variable inductance L1 may be serial coupled between the coil winding 434 and a local ground potential to set resonance of this sensor circuit. FIG. 31D shows another resonance change sensor circuit in which the traverse separation between a pair of capacitive plates 438 is controlled by motion of a reciprocating element 421. Resonance is set initially by an inductance L2 coupled in parallel with the capacitance of the two plates 438. A variable capacitance is created by the two plates 438. A variable capacitance C13 may be serially coupled between the plates 438 and a local ground potential to set the initial resonant frequency. Change in the capacitance of the plates 438 is detected by a convertor 436 which is, in turn, coupled to a buffer amplifier A1. FIG. 31E shows a piezoelectric strain gauge 440 producing a differential voltage in response to motion of a reciprocating element 421. The differential voltage is applied across the input terminals of an operational amplifier stage A12 which, in turn, supplies an output to a voltage comparator stage A13.

Several modifications may be made to adapt the principles of the puncturing instrument 10 to particular applications. For example, the inner sleeve 56 and the outer sleeve 12 may be made of a flexible material instead of a rigid material such as stainless steel, to accommodate an implement 40 made of a flexible material. Also, as illustrated in the partially cut-away front view of FIG. 28B and the front assembly view of FIG. 28C, the instrument may be made without a valve assembly chamber 20, particularly where the shaft 42 of the puncturing implement is hollow (e.g., a needle). In such an application an end cap 28 bearing a threaded distal end 26' may be screwed into the threaded receiving proximal end 17 of the outer sleeve 11 to compress the bias spring 66 against the proximal end flange 58 of the inner sleeve 56. After the implement has penetrated the wall of a cavity such as a blood vessel, a syringe (not shown) may be connected directly to a suitable fitting 52' on the proximal end of the implement.

In the embodiment shown in FIG. 2C, the slight bearing surface 60 formed by the distal end of the inner sleeve recedes completely into the distal end 15 of the outer sleeve. By inserting a small shim inserted at either end of spring 66 will prevent the inner sleeve from completely receding so that its distal end 60 will provide a smooth transition between the distal shaft end 44 and the outer sleeve end 15 in the manner shown in FIG. 2B. Alternately, the distal end of the inner sleeve may form a sloped rim 60' to provide a smooth transition and thereby facilitate penetration of the inner and outer sleeves through a puncture wound.

A Pressure sensor or transducer element 442 may be fitted directly into the blade or beveled distal end 443 of a puncturing implement as shown in FIG. 32, to sense the pressure occurring on the distal end of implement during penetration due to resistance by the tissues and membranes of the cavity wall. A pair of electrical leads 444 couple the element 442 to an electrical socket 90 at the proximal implement end. A small battery powered electronic circuit 446 capable of emitting a low power, radio frequency signal may be mounted on an electrical plug 92 and electrically coupled to the sensor element 442 via the socket 90 and leads 444. As the distal end 442 is forced into a cavity wall, skin, tissues and membranes exert a counterforce upon the sensor, thereby causing circuit 446 to generate a ready signal which may be received and converted into an audio frequency (e.g., an intermittent tone) or visible signal by a receiver coupled to an alarm network 110. The tissue and membrane continue to a counterforce on the distal end during penetration. As the distal end 443 passes through the cavity wall and into the cavity interior, the counterforce on the sensor is suddenly removed, causing the circuit 446 to generate a puncture completed signal to the receiver and alarm network. This signal will alert a surgeon or nurse to immediately stop forcing the implement into the puncture wound. The transmitter may then be removed from the electrical socket 90 and a catheter 448 connected to an orifice 450 at the proximal end of the implement. The combined receiver and alarm circuit 110 may be packaged in a small box and carried in a smock pocket of a surgeon (e.g., or a nurse in an IV team, for example). The radio frequency link between the puncturing implement 400 and the alarm circuit eliminates the need to use a sterile set of electrical leads 202. The link additionally permits a single transmitter to be used with many surgical puncturing instruments and implements in making different punctures in different patients (e.g., for IV needles) during the course of a day without having to remove and reconnect the receiver and alarm networks prior to making each puncture.

Figure 33:
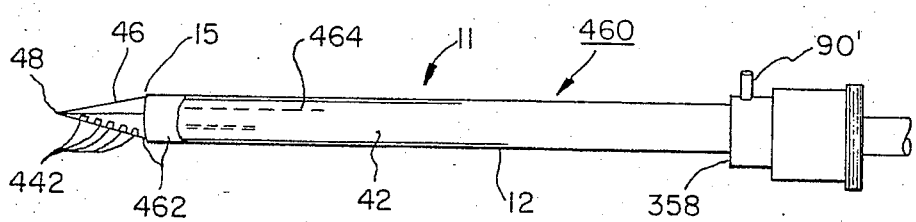
FIG. 33 shows an alternative embodiment of a cavity puncturing instrument having discrete pressure sensitive elements separately fitted into both its sleeve and the blade of its implement.

As shown in the alternative embodiment of FIG. 33, a single sleeve puncturing instrument 460 may be constructed with one or more pressure sensors or transducers 442, 462 fitted into both the blade 46 of a puncturing implement and the distal end 15 of the sleeve, respectively. Sets of electrical leads 444 and 464 running through the implement shaft 42 and the instrument sleeve 12, respectively, couple the implement and sleeve sensors 442, 462 to a multiterminal socket 90' at the proximal end of the instrument sleeve 12. A set of sliding electrical contacts between the outer surface of the implement shaft 42 and inner surface of instrument sleeve allow continuous contact between the implement sensor leads 464 and the electrical contact 90 during axial movement of the implement within the sleeve. When the distal sleeve end 15 is held against a cavity wall, the sleeve sensors 462 would provide a first signal condition. As the blade 46 of the implement is forced into the cavity wall, the implement sensors 442 sequentially each provide a set of second signals indicating the occurrence of penetration. When the implement's point 48 breaks through the cavity wall, pressure created by resistance of tissue and membranes is sequentially removed from the blade sensors 442, causing a third set of signals, indicative of the near completion of the puncture. Then, as the distal sleeve end follows the blade through the cavity wall, the sudden absence of resistance decreases pressure on the sleeve sensors 462, causing a fourth signal condition, indicative of completion of the puncture. The use of sensors in both the blade 46 and sleeve 12 permits an expanded alarm network to provide a surgeon with a sequence of sensible signals indicative of the progress of an instrument during the process of penetration. The array of blade sensors 442, for example, may be used to sequentially trigger audible tones of progressively higher frequency in an expanded alarm network.

Figure 34:
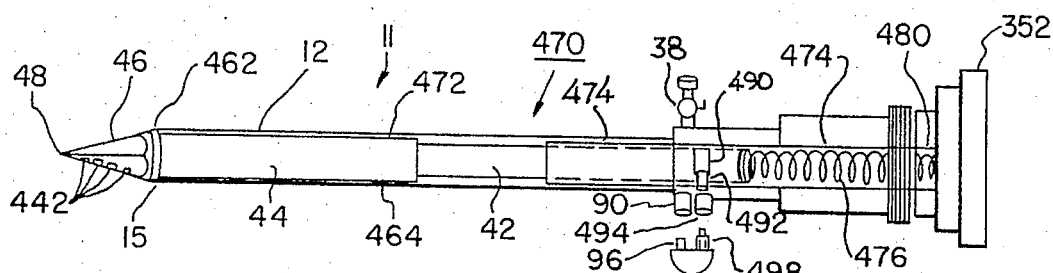
FIG. 34 shows an alternative embodiment of a cavity puncturing instrument having a spring-loaded implement which may be automatically withdrawn into a puncturing instrument sleeve.
Figure 35:
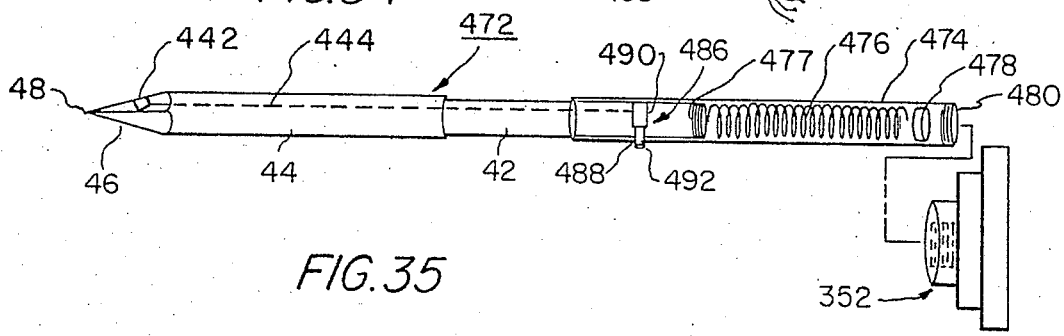
FIG. 35 shows a detailed, partially cut-away view of the puncturing implement shown in FIG. 34.

Alternative embodiments 470 of a single sleeve puncturing instrument are illustrated in FIGS. 34 and 35, each having a two-part, internally retractible puncturing implement 472. The implement of each instrument has a shaft with a greater diameter section 44 at its distal end terminating in a sharp, multi-sided blade 46 and point 48 bearing one or more pressure sensors or transducer elements 442. The intermediate section of the implement's shaft 42 of reduced diameter, is able to slide within a hollow proximal tubular section 474. A coiled tension spring 476, shown extended, has opposite ends attached to the proximal end 477 of intermediate shaft section 42 and a threaded plug 478 in the proximal end 480 of the tubular section 474. The intermediate shaft section 42 contains a detent mechanism 486 holding a small detent 488 urged radially outward by a compression spring 490. When the intermediate shaft section is fully extended axially outward from the tubular section 474, detent 488 is coaxially aligned with and protrudes through a small hole 492 in the wall of the tubular section, thereby locking the intermediate shaft section in the fully extended position shown. Electrical leads 444 passing through the interior of the distal and intermediate sections 44, 42 are couple the blade pressure sensors 442 to electrical contacts within the detent 488. Electrical leads 464 passing along the instrument sleeve 12 couple pressure sensors 462 fitted into the distal end of the sleeve with electrical socket 90.

Preparatory to use, the distal and intermediate sections of the implements 472 are pulled axially outward from the tubular section until detent 488 engages and passes through detent hole 492. The handle assembly 352 is then attached to the proximal end 480 of the tubular section and the distal end 44 of the implement are inserted through the gate valve (not shown) and sleeve 11 of the instrument. When fully inserted into the sleeve, detent 488 is coaxially aligned with a radial solenoid socket 494 adjacent the electrical socket 90. An electrical plug assembly 496 contains an electrical jack 96 to couple the sleeve sensors 462 to an expanded alarm network and a solenoid 498 having electrical contacts to couple the blade sensors 442 via leads 444 and the contacts carried by the detent 488 through solenoid socket 494 to the alarm network in parallel with the sleeve sensors. The plug assembly also carries a set of electrical leads coupling solenoid 498 to the alarm network. When the blade 46 of the implement is pressed against a cavity wall, the counterforce exerted by the skin, tissues and membranes on the pressure sensors 442 in the blade trigger the alarm network with a sequential set of ready signals. Counterforce subsequently exerted on the sleeve sensors 462 which provides the alarm network with a second signal may be used to verify this indication. Disappearance of the counterforce against the blade sensors 442 as the blade passes into the cavity interior provides the alarm network with a sequential set of signals which may be used as an indication of the near completion of the puncture. Referring briefly to the schematic of the network 110' shown in FIG. 30, it may be noted that the third signal set may be applied to control the base of NPN transistor Q2 and, via the collector lead of transistor Q2, the base of PNP transistor Q3, thereby energizing the coil of solenoid 498. Energization of the solenoid causes its plunger to depress detent 498, thereby releasing the intermediate shaft section 42 and permitting tension spring 476 to retract the intermediate and distal sections 42, 44 of the implement towards the proximal end 489 of the implement. This action effectively causes the spring 476 to withdraw the implement blade 46 and point 48 within the instrument sleeve 11, shielding the anatomical structure within the cavity for inadvertent contact with the blade. Subsequent disappearance of counterforce against the sleeve sensors 462 as the distal end 15 of the sleeve passes into the cavity interior provides the alarm network with a fourth signal which indicates completion of the puncture. The fourth signal may be used to light diode emitting diode N3 and switch speaker T1 from an intermediate audio beeping stage A11 to a continuous wave audio signal stage A7, thereby alerting a surgeon to completion of the puncture.

Figure 36:
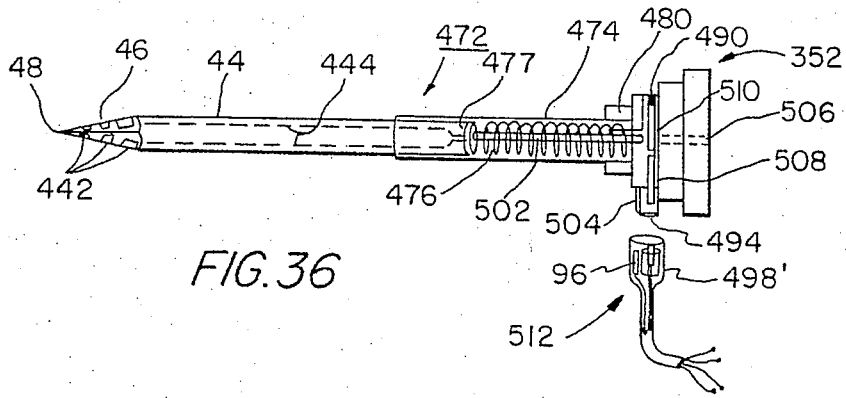
FIG. 36 shows a cut-away view of an alternative embodiment of a puncturing implement suitable for use within a conventional puncturing instrument sleeve.

An alternative configuration of the puncturing implement 472, illustrated in FIG. 36, has the implement shaft 44 terminating at its proximal end in a long rod 502. A coiled tension spring 476 is stretched with its opposite ends attached to the proximal end 477 and the proximal end 480 of the tubular section. Electrical leads 444 from an array of pressure sensors 442 fitted into the blade 46 of the implement pass through the shaft 44 and rod 502 to make sliding contact along a proximal section of the rod with a set of electrical connectors 504 that radially protrude through the implement handle 352. The handle has an axial passage 506 coaxially aligned with rod 502. Protrusion of rod 502 through passage 506 is blocked by a bar 508 held in position by a small compression spring 490. The bar contains an aperture 510 which permits axial passage of rod 502 when the bar is forced against the spring 490. An electrical plug assembly 512 contains an electrical jack 96 to couple sliding contact connectors 504 to an alarm network and a contactless solenoid 498' to solenoid port 494 in the implement handle 352. Upon cessation of counterforce against the blade sensors 442, the signal transmitted via leads 444, contacts 504 and jack 96 to a suitably programmed alarm network solenoid 498' may be energized to depress bar 508 against spring 490, thereby aligning aperture 510 with handle passage 506. This action permits tension spring 476 to pull the proximal shaft end 477 toward the proximal tubular section end 480, causing the sharp implement blade 46 and point 48 to retract into an instrument sleeve 11.

Figure 37:
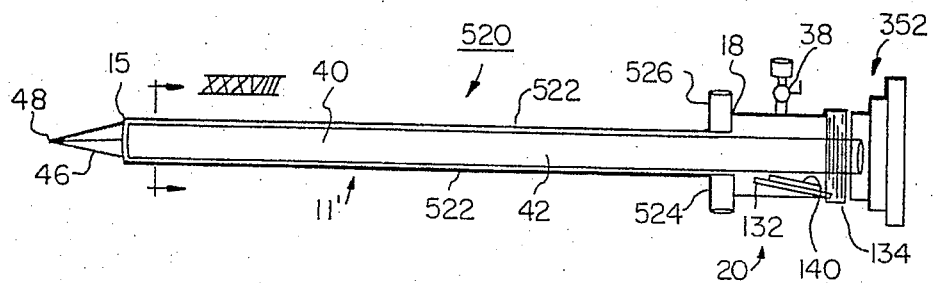
FIG. 37 shows a cut-away view of an alternative embodiment of a puncturing instrument containing a sheath of fiber optic cables within its sleeve.
Figure 38:
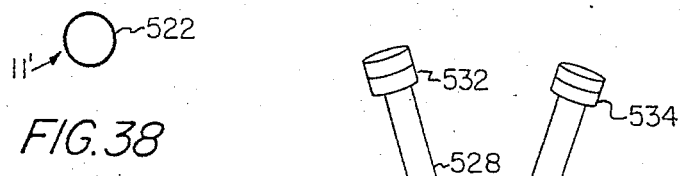
FIG. 38 shows a sectional end view of the trocar sleeve and fiber optic cable sheat along line XXXVIII in FIG. 37.
Figure 39:
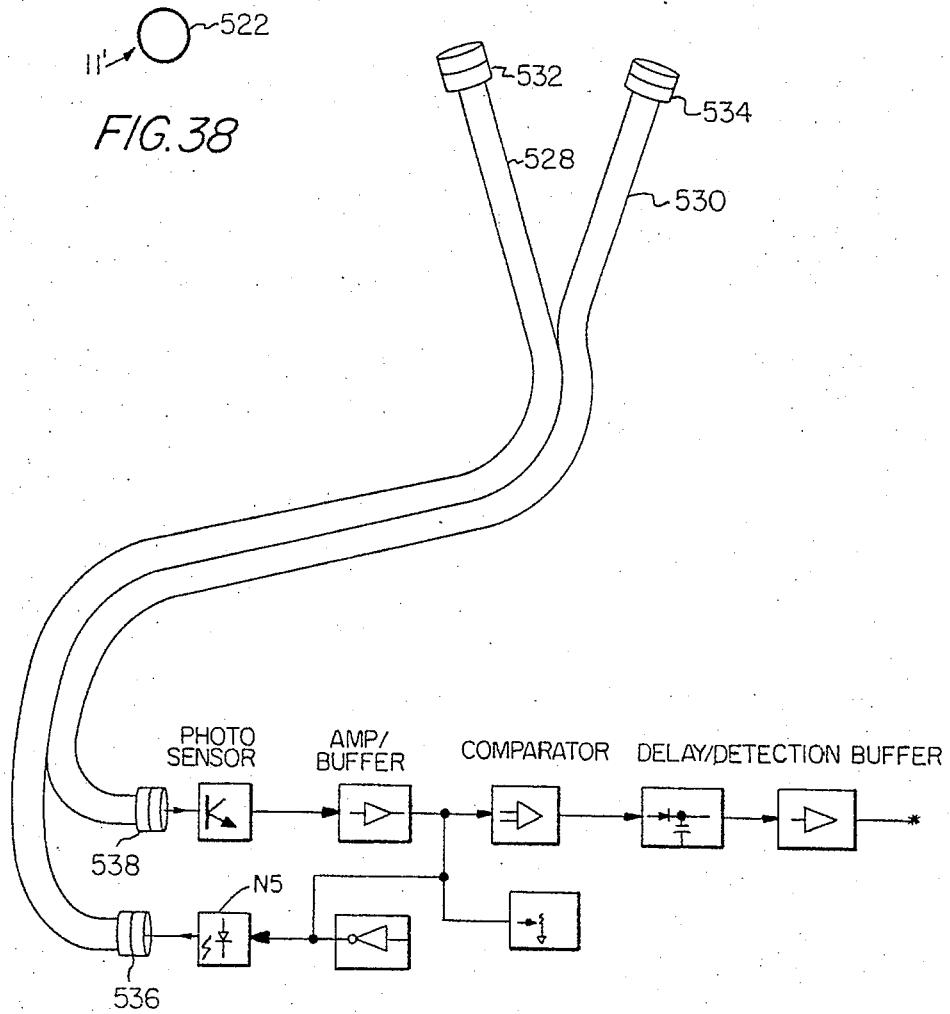
FIG. 39 is a schematic block diagram of a fiber optic cable harness and light emitting and detection circuit connectable via the cable harness to the puncturing instrument shown in FIG. 37.

Another alternative embodiment, illustrated in FIG. 37, has a sleeve 11' fitted with fiber optic cables 522 extending axially along its length. As shown in the cross-sectional view of FIG. 38, the cables 522 effectively form a sheath around the inside circumference of sleeve 11', terminating a short distance from the distal sleeve end 15. A pair of fiber optic cable couplers 524, 526 are positioned in diametrically opposite locations at the proximal end 18 of the sleeve. Every other fiber optic cable in alternate pairs around the circumference of the sheath terminates in one of the couplers 524; the remaining half of the cables are connected to the other coupler 526. A pair of fiber optic cable harnesses 528, 530 have couplers 532, 534 at one end for optically mating the cables in the harnesses via couplers 524, 526, to the sleeve cables 522. Similar couplers 536, 538 at the opposite ends of the cable harnesses connect the cable harnesses 528, 530 to a light source (e.g., an infrared light emitting diode) and to a photodetector (e.g., a photoconductor or a photovoltaic cell) in a remote alarm network. When the alarm network is connected to the instrument 520 by a cable harness pair, light from the source travels via couplers 536, 532, 526, and cable harness 528, through one-half of the fiber optic cables 522 to the distal end 15 of the sleeve 11. During penetration, the distal sleeve end 15 is pressed tightly against membrane and tissue of the cavity wall, blocking emission of light emitted by one-half of the sleeve cables 522 from the distal sleeve end. A significant percentage of this trapped light is reflected from the membrane and tissue and conveyed by the non-emitting cables 522 via couplers 524, 534, 538 and cable harness 530 to the photodetector in the alarm network. The alarm network may be constructed to provide a ready signal (e.g., an intermittent tone) during conditions of high reflectivity. As distal sleeve end 15 passes through the cavity wall and into the cavity interior, the absence of membrane and tissue allows light emitted by one-half of the sleeve cables 522 to radiate from the distal sleeve end 15 into the cavity interior, creating a condition of low reflectivity. Lowered reflectivity is evidenced by diminished intensity of light conveyed by the non-emitting cables to the photodetector. The alarm network may be constructed to provide a ready signal (e.g., an intermittent tone) during conditions of high reflectivity and a puncture completed signal (e.g., a steady tone) in response to the sudden diminution of reflectivity occurring as distal sleeve end 15 enters the cavity interior.

The puncturing instrument disclosed may be used to provide communication through the walls of various anatomical cavities in human and animal patients. By selecting a suitable length and diameter for the instrument and the implement which it accommodates (e.g., trocar, cannula or needle), the instrument may be made suitable for puncturing the walls of such cavities as a blood vessel, a spinal cavity, a subarachnoid space, an ear ventricle, an abdominal cavity, or a joint cavity. After piercing a cavity wall, a needle implement, for example, may be left in place and used to inject or withdraw gases or liquids from the cavity. The bias force exerted by the spring 66 on the inner sleeve 56 or the obstruction members 354, 402 may be selected before puncturing an anatomical structure in order to correlate the bias force to the composition, muscle tone, and hardness of the tissue forming the cavity wall.

In constructing an instrument 10 for a particular surgical application, either the width of the inner sleeve flange 58 or the location of the tactile sensor tip 76 of the plunger 96 of the electrical switch may changed to modify the sequence of the alarm network. Additionally, more than one switch or tactile sensor may be incorporated into an instrument.

Also, the piezoelectric strain gauge elements may be made of silicon, germanium quartz, ammonium-dihydrogen-phosphate, or an electrostrictive material such as barium titanate or lead zirconate.

The instruments disclosed herein provide a reciprocating inner sleeve which automatically recedes into an outer sleeve in response to counterforce exerted by a cavity wall on the blunt bearing surface of the inner sleeve, thereby exposing the cavity wall to the sharp distal blade of a puncturing implement. Then, as the blade of the implement passes through the cavity wall and into the cavity, the junction between the distal ends of the outer sleeve and recessed inner sleeve passes through the cavity wall, thereby releasing to inner sleeve from counterforce, allowing it to automatically resume its former position shielding the sharp blade and the inner anatomical structure from inadvertent contact. Preferably, the bearing surface of the inner sleeve and the distal end of the outer sleeve define right angles to their longitudinal axes. Additionally, recision and protrusion of the inner sleeve may be monitored with the aid of tactile sensors as well as electronic sensors coupled to a network for generating one or more visual or audio signals indicative of either axial movement of axial location of the inner sleeve relative to the outer sleeve. Alternatively, the puncturing implement itself may include a member biased to protrude from an opening in the side or edge of its blade and to extend beyond the point of the blade in the manner of the trocars shown in FIGS. 20, 22, 24 or 25 for example, or in the manner of the modified needle of FIG. 27, thereby obstructing the point from inadvertently pricking, grazing or piercing an interior anatomical structure. A handle, either carrying merely a sensor switch or a battery, electronic alarm network, audio generator and speaker as well as a sensor switch may be attached to the proximal end of the implement to monitor recision and protrusion of the obstructing member.

I claim:

1. A surgical instrument for providing communication through an anatomical organ structure, comprising:
    means providing a first lumen for accommodating longitudinal interior passage of a shaft of an elongate implement, said elongate implement having a proximal section exhibiting a transverse cross-sectional dimension greater than the transverse cross-sectional dimension of said shaft and a distal end, said accommodating means including means having an abutment surface for preventing passage of said proximal section through said first lumen;
    shielding means providing a second lumen permitting longitudinal interior passage of said elongate implement through said second lumen and having a distal end terminating in a bearing surface open to longitudinal passage of said elongate implement, for reciprocating longitudinally inside said first lumen between said accommodating means and said shaft while said proximal section of said elongate implement is held against said abutment surface; and
    means positionable between said accommodating and shielding means for biasing said bearing surface to protrude beyond the distal end of said first lumen and for permitting a section of said shielding means to recede into said first lumen while said proximal section of said elongate implement is held against said abutment surface when said bearing surface is subjected to force along its longitudinal axis, whereby said shielding means obstructs anatomical members from making inadvertent contact with the distal end of said elongate implement when said distal end of said implement is extended beyond said distal end of said first lumen.

2. The instrument of claim 1 wherein said bearing surface forms a flush transition between the circumference of said shaft and the distal exterior of said accommodating means when said section of said shielding means recedes towards said accommodating means distal end.

3. The instrument of claim 1 wherein said bearing surface forms a transition between the circumference of said shaft and the distal exterior of said accommodating means when said section of said shielding means recedes towards the distal end of said accommodating means.

4. A surgical instrument for providing communication through an anatomical organ structure, comprising:

means having a shaft, a proximal section exhibiting a transverse cross-sectional dimension greater than the cross-sectional dimension of said shaft and a sharp distal end, for puncturing an anatomical structure when subjected to a force directed toward said sharp distal end along the longitudinal axis of said shaft;

means having a length less than the length of said puncturing means, including a first lumen, for accommodating longitudinal interior passage of said puncturing means through said first lumen, said accommodating means including an abutment surface for preventing passage of said proximal section of said puncturing means through said first lumen;

shielding means providing a second lumen permitting longitudinal interior passage of said shaft inside said second lumen and having a bearing surface at its distal end protrusible beyond the distal end of said first lumen, for reciprocating longitudinally within said first lumen between said accommodating means and said shaft while said proximal section of said shaft is held against said abutment surface; and means contacting said shielding means for biasing said bearing surface to protrude beyond said distal end of said first lumen and permitting a section of said shielding means to recede towards the proximal end of said accommodating means when said bearing surface is subjected to force along its longitudinal axis, whereby said shielding means obstructs anatomical members from making inadvertent contact with the distal end of said shaft when said sharp distal end is extended beyond said distal end of said first lumen.

5. The instrument of claim 4 wherein said bearing surface forms a transition between the circumference of said shaft and the distal exterior of said accommodating means when said section of said shielding means recedes towards the distal end of said accommodating means.

6. The instrument of claim 4 wherein said bearing surface is open to longitudinal passage of said shaft.

7. The instrument of claim 4 wherein said bearing surface forms a flush transition between the circumference of said shaft and the distal exterior of said accommodating means when said section of said shielding means recedes towards said accommodating means distal end.

8. The instrument of claims 1 or 4 wherein said bearing surface is open to longitudinal passage of said shaft when said section of said shielding means recedes towards said accommodating means proximal end.

9. The instrument of claims 1 or 4 wherein said accommodating and shielding means conjunctively have a length greater than said shaft when said section of said shielding means fully protrudes beyond said first lumen distal end and a length less than said shaft when said section of said shielding means fully recedes towards said accommodating means distal end.

10. The instrument of claims 1 or 4 wherein said bearing surface is receivable within said accommodating means distal end when said bearing surface is subjected to force along its longitudinal axis.

11. The instrument of claim 10 wherein said bearing surface is receivable within said first lumen when said section of said shielding means recedes towards said accommodating means proximal end.

12. The instrument of claim 10 wherein said bearing surface protrudes from said first lumen when said section of said shielding means fully recedes towards said accommodating means proximal end.

13. The instrument of claims 1 or 4 wherein said implement has a stop surface limiting longitudinal passage of said implement when said abutment surface is in contact with said stop surface.

14. The instrument of claim 13 wherein said accommodating means is stationary relative to said shaft while said abutment surface and said stop surface are in contact.

15. The instrument of claim 14 wherein said shielding means includes a sleeve defining said second lumen and the distal end of said sleeve is perforated.

16. The instrument of claim 13 wherein said shielding means is axially reciprocatable between said accommodating means and said shaft while said abutment surface and said stop surface are in contact.

17. The instrument of claim 16 wherein said shielding means includes a sleeve defining said second lumen and the distal end of said sleeve defines a blunt rim forming said bearing surface.

18. The instrument of claims 1 or 4 wherein said accommodating means comprises a first sleeve defining said first lumen.

19. The instrument of claim 18 wherein said shielding means comprises a second sleeve defining said second lumen.

20. The instrument of claim 18 wherein said shielding means includes a second sleeve defining said second lumen, the distal end of said second sleeve defines a rim and said rim tapers radially inward to form a close fit around said shaft.

21. The instrument of claims 1 or 4 wherein said biasing means comprises a spring disposed inside said accommodating means against the proximal end of said shielding means.

22. The instrument of claim 1 or 4 wherein said bearing surface and the distal end of said accommodating means define planes normal to the longitudinal axis of said shielding means and accommodating means.

23. The instrument of claim 1, 4, 6 or 7 further comprising means carried by said accommodating means and contacting said shielding means for following axial movement of said shielding means relative to said accommodating means and for creating a sensible condition in response to said axial movement.

24. The instrument of claim 23 wherein said following means creates a sensible condition having a first state upon recision of said section of said shielding means and a second state upon protrusion of said section of said shielding means.

25. The instrument of claim 24 wherein said shielding means includes a longitudinal segment varying in transverse dimension and said following means is connected to said accommodating means to ride along said longitudinal segment of said shielding means.

26. The instrument of claim 25 wherein said following means extends from said longitudinal segment through said accommodating means to provide tactility sensible indications of said first and second states.

27. The instrument of claim 26 wherein said following means comprises an element having one end encircling the outer circumference of said accommodating means to bias the outer end of said element via an intermediate section to extend radially inward through said accommodating means to the ride along said shielding means longitudinal segment.

28. The instrument of claim 26 wherein said following means includes a plurality of electrical contacts and an actuator positioned to ride along said longitudinal segment and toggle said contacts between electrically opened and closed conduction conditions in response to variation of said longitudinal segment transverse dimension.

29. The instrument of claim 28 further comprising an electrical network connectable to said contacts for generating a signal indicative of said first and second states.

30. The instrument of claim 29 wherein said network includes means for providing a visually sensible signal.

31. The instrument of claim 29 wherein said network includes means for providing an aurally sensible signal.

32. The instrument of claim 29 wherein said network includes means for providing visually and aurally sensible signals.

33. A surgical instrument for providing communication through an anatomical organ structure, comprising:
  means having an abutment member and shaft longitudinally accommodatable within an outer sleeve, longitudinal movement of said shaft inside said sleeve being limited by contact of said abutment member with said sleeve, said shaft having a distal end with a distal blade surface tapering into a sharp distal point, said distal blade surface being perforated along one side by an aperture, for puncturing an anatomical organ structure when subjected to force along the longitudinal axis of said shaft;
  means having a blunt distal bearing surface, slidably extending through said aperture, for reciprocating through said aperture while said abutment member is in stationary contact with said sleeve;
  means positionable between said puncturing means and said reciprocating means for biasing a distal section of said reciprocating means to protrude beyond said aperture and permitting said distal section of said reciprocating means to recede into said aperture when said bearing surface is subjected to force along its longitudinal axis, whereby when said distal section of said reciprocating means is protruding beyond said distal point of said blade surface, said bearing surface obstructs anatomical members from making inadvertent contact with said distal point of said blade surface; and
  means connectible to the proximal end of said puncturing means for responding to longitudinal movement of said reciprocating means relative to said puncturing means and creating a sensible signal having one state upon recision of said distal section of said reciprocating means into said aperture and another state upon protrusion of said distal section of said reciprocating means from said aperture.

34. A method for providing communication through an anatomical organ structure, comprising the steps of:
  biasing an axial reciprocating member having a distal end bearing surface to assume a rest position with said bearing surface extending beyond the distal end of an elongate member encircling and receiving said bearing surface;
  inserting an elongate implement having a sharp distal end axially into said elongate member and said reciprocating member until said sharp distal end is positioned inside said bearing surface and inside said elongate member distal end;
  placing said reciprocating member against the cavity wall of an anatomical organ structure;
  pushing said reciprocating member against the cavity wall until said reciprocating member assumes a suspense position between said elongate member and said elongate implement wherein said sharp distal end touches said cavity wall;
  forcing said sharp distal end through said cavity wall until said bearing surface reaches the boundary between said cavity wall and the interior of said cavity; and
  permitting said reciprocating member to assume said rest position within the interior of said cavity.

35. The method of claim 34 further comprising the step of providing a signal upon movement of said reciprocating member between said rest and suspense positions.

36. The method of claim 34 further comprising the step of providing a first signal upon movement of said reciprocating member from said rest position to said suspense position.

37. The method of claim 36 further comprising the step of providing a second signal upon movement of said reciprocating member from said suspense position to said rest position.

38. The method of claim 34 further comprising the step of selecting the force for biasing said reciprocating member in correlation with the hardness of the tissue forming said cavity wall.

39. A surgical instrument for providing communication through an anatomical organ structure, comprising:
  means having an interior lumen terminating in an open distal end for accommodating axial reciprocation of an elongate implement of lesser cross-sectional dimension;
  means adjoining the proximal end of said accommodating means for providing a chamber opening at its distal end into said lumen and permitting axial reciprocation of said elongate implement, said chamber, having an open proximal end including a valve seat; and
  means having a unitary structure with a flexible central region forming a cavity concavely oriented outward from said chamber proximal end and having a distal region within said cavity perforated by at least one slot and a plurality of flaps axially extending from opposite sides of said slot, said flaps having a rest configuration in which said flaps mate together and extend axially into said chamber and terminate the distal region of said cavity and a distended configuration allowing passage of said elongate implement through said slot, and a rim resting against said valve seat, for sealing the proximal end of said chamber against passage through said chamber of gaseous and liquid phase effluent from said lumen of said accommodating means.

40. The instrument of claim 39 wherein said distal region of said sealing means forms arcuate edges on opposite sides of said slot and a pair of said flaps adjoin said arcuate edges of said slot.

41. The instrument of claim 39 wherein said sealing means has a pair of flaps defining substantial planes flexibly adjoining the convex surface of said distal region along opposite arcuate edges of a single deformable slot in said distal region.

42. The instrument of claim 39 wherein said sealing means has a plurality of flaps longitudinally separated by an equal plurality of longitudinal slots, further comprising elastic means encircling said flaps for holding said flaps in a normally mated array.

43. A surgical instrument for providing communication through an anatomical organ structure, comprising:
   means having an interior lumen terminating in an open distal end for accommodating axial reciprocations of an elongate implement of lesser cross-sectional dimension;
   means adjoining the proximal end of said accommodating means for providing a chamber having an opening at its distal end into said lumen, said opening extending transversely across the axis of said lumen and permitting axial reciprocation of said elongate instrument; and
   means positioned within said chamber to reciprocate transversely to the longitudinal axis of said lumen and having exterior peripheral surfaces conforming to the dimensions of said chamber extending transversely to said lumen and radially opposed separable mating surfaces and a wedged surface oriented along said longitudinal axis facing toward the proximal end of chamber, for closing said proximal end of said chamber to passage of gaseous and liquid phase effluent when said opposed surfaces are mated together within said chamber.

44. The instrument of claim 43 further comprising a plurality of resilient members within said chamber for holding said separable surfaces together in the absence of said elongate implement.

45. The instrument of claim 43 wherein said closing means comprise a pair of members exhibiting opposite magnetic polarities at said separable surfaces.

46. A surgical instrument for providing communication through an anatomical organ structure, comprising:
   means having an elongate interior lumen for accommodating axial reciprocation of an implement shaft extending beyond the distal end of said lumen;
   first means extending from a proximal section of said accommodating means towards the distal end of said lumen for transmitting radiant energy to and emitting radiant energy at said lumen distal end; and
   second means extending from said proximal section of said accommodating means towards said distal end of said lumen for receiving and conducting to said proximal section of said accommodating means radiant energy emitted by said first transmitting means;
   said first and second means forming an annular sheath around the interior periphery of said interior lumen, said sheath providing a second lumen accommodating said axial reciprocation of said implement shaft beyond the distal ends of said lumen and said sheath.

47. A surgical instrument for providing communication through an anatomical organ structure, comprising:
   means having an elongate shaft exhibiting a longitudinal axis and terminating in a sharp, distal end, for puncturing the cavity wall of an anatomical organ structure;
   means borne by said puncturing means distal end for converting counterforce exerted by said cavity wall against said distal end into transmissible energy;
   means connected to said converting means for conveying said transmissible energy toward the proximal end of said puncturing means;
   means having an interior bore coaxially aligned with the longitudinal axis of said shaft for receiving said puncturing means proximal end;
   means for biasing said puncturing means proximal end to withdraw into said interior bore;
   means interposed between said puncturing means proximal end and said interior bore assuming a normally protruding position for determining said puncturing means proximal end extended from said interior cavity in opposition to said biasing means.

48. A surgical instrument for providing communication through an anatomical organ structure, comprising:
   means including a first sleeve defining a first lumen for accommodating longitudinal interior passage of a shaft of an elongate implement terminating in a sharp distal section;
   shielding means including a second sleeve having a distal section defining a second lumen permitting longitudinal interior passage of said shaft through said second lumen, said distal section terminating in a bearing surface open to axial passage of said elongate implement, and the end of said distal section tapering radially inward to form a close fit around said shaft, for reciprocating axially within said first lumen between said accommodating means and said shaft; and
   means positionable between said accommodating and shielding means for biasing said bearing surface to protrude beyond the distal end of said first lumen and permitting said distal section of said shielding means to recede into said first lumen when said bearing surface is subjected to force along its longitudinal axis.

49. The instrument of claim 48 wherein said section of said shielding means is perforated.

50. A surgical instrument for providing communication through an anatomical organ structure, comprising:
   means having a shaft terminating in a sharp distal end for puncturing an anatomical structure when subjected to force along the longitudinal axis of said shaft;
   means having a length less than a length of said puncturing means, including a first sleeve defining a first lumen for accommodating longitudinal interior passage of said puncturing means through said first lumen;
   shielding means including a second sleeve defining a second lumen permitting longitudinal interior passage of said shaft inside said second lumen, having a bearing surface at its distal end protrusible beyond the distal end of said first lumen, said bearing surface tapering radially inward to form a close fit around said shaft, for reciprocating longitudinally within said first lumen between said accommodating means and said shaft; and
   means contacting said shielding means for biasing a section of the distal end of said shielding means to protrude beyond the distal end of said first lumen and permitting said section of said shielding means to recede towards the proximal end of said accommodating means when said bearing surface is subjected to force along its longitudinal axis.

51. The instrument of claim 50 wherein said section of said shielding means is perforated.

52. A surgical instrument for providing communication through an anatomical organ structure, comprising:

means providing a first lumen for accommodating longitudinal interior passage of a shaft of an elongate implement having a distal end;

shielding means having a perforated distal section defining a second lumen permitting longitudinal interior passage of said elongate implement through said second lumen, said perforated distal section terminating in a bearing surface open to longitudinal passage of said elongate implement, for reciprocating longitudinally inside said first lumen between said accommodating means and said shaft; and means positionable between said accommodating and shielding means for biasing said bearing surface to protrude beyond the distal end of said first lumen and for permitting said perforated distal section to recede into said first lumen when said bearing surface is subjected to force along its longitudinal axis.

53. A surgical instrument for providing communication through an anatomical organ structure, comprising:

means having a shaft with a sharp distal end for puncturing an anatomical structure when subjected to a force along the longitudinal axis of said shaft;

means having a length less than the length of said puncturing means, including a first lumen, for accommodating longitudinal interior passage of said puncturing means through said first lumen;

shielding means having a perforated distal section defining a second lumen permitting longitudinal interior passage of said shaft inside said second lumen, said distal section terminating in a bearing surface protrusible beyong the distal end of said first lumen for reciprocating longitudinally within said first lumen between said accommodating means and said shaft; and means contacting said shielding means for biasing said perforated distal section of said shielding means to protrude beyond said first lumen distal end and permitting said perforated distal section to recede towards the proximal end of said accommodating means when said bearing surface is subjected to force along the longitudinal axis of said shielding means.

54. The instrument of claim 48, 49, 52 or 53 further comprising means carried by said accommodating means, for following axial movement of said shielding means relative to said accommodating means and for creating a sensible condition in response to said axial movement.

55. The instrument of claim 54 wherein said following means creates a sensible condition having a first state upon recision of said section of said shielding means and a second state upon protrusion of said section of said shielding means.

* * * * *

UNITED STATES PATENT AND TRADEMARK OFFICE
Certificate

Patent No. 4,535,773                                                                                 Patented: August 20, 1985

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: InBae Yoon, Phoenix, Md.; and Young Jae Choi, Towson, Md.

Signed and Sealed this Second Day of June, 1998.

WYNN WOOD COGGINGS, *SPE*
Art Unit 3734